US006916653B2

(12) United States Patent
Eagles et al.

(10) Patent No.: US 6,916,653 B2
(45) Date of Patent: Jul. 12, 2005

(54) RIBOZYMAL NUCLEIC ACID

(75) Inventors: Peter Anthony Minter Eagles, Bromley (GB); Richard Qihao Zheng, London (GB)

(73) Assignees: King's College London, London (GB); Queen Mary and Westfield College, London (GB)

( * ) Notice: Subject to any disclaimer, the term of this patent is extended or adjusted under 35 U.S.C. 154(b) by 272 days.

(21) Appl. No.: 09/880,821

(22) Filed: Jun. 15, 2001

(65) Prior Publication Data

US 2002/0061585 A1 May 23, 2002

Related U.S. Application Data

(63) Continuation of application No. 09/617,505, filed on Jul. 14, 2000, now abandoned, which is a continuation of application No. PCT/GB99/00134, filed on Jan. 15, 1998.

(30) Foreign Application Priority Data

Jan. 15, 1998 (GB) .............................................. 9800870
Dec. 23, 1998 (GB) .............................................. 9828659

(51) Int. Cl.$^7$ .......................... C12P 19/34; C12N 15/00; C07H 21/02; C07H 21/04

(52) U.S. Cl. ................ 435/320.1; 435/91.1; 435/91.31; 435/91.4; 536/23.1; 536/24.5

(58) Field of Search .......................... 435/6, 91.1, 91.4, 435/91.31, 455, 458, 320.1; 514/44; 536/23.1, 24.5; 436/23.1, 24.5

(56) References Cited

U.S. PATENT DOCUMENTS

| | | |
|---|---|---|
| 4,987,071 A | 1/1991 | Cech et al. |
| 5,037,746 A | 8/1991 | Cech et al. |
| 5,093,246 A | 3/1992 | Cech et al. |
| 5,116,742 A | 5/1992 | Cech et al. |
| 5,354,855 A | 10/1994 | Cech et al. |
| 5,591,610 A | 1/1997 | Cech et al. |
| 5,594,122 A | 1/1997 | Friesen |
| 5,910,628 A | 6/1999 | Miller et al. |
| 5,939,538 A | 8/1999 | Leavitt et al. |
| 6,025,154 A | 2/2000 | Li et al. |

FOREIGN PATENT DOCUMENTS

| | | |
|---|---|---|
| EP | 291533 B | 10/1995 |
| WO | 97/45543 | 4/1997 |
| WO | WO 97/17433 | 5/1997 |
| WO | 97/28258 | 7/1997 |
| WO | WO 97/41243 | 11/1997 |
| WO | WO 97/44055 | 11/1997 |
| WO | WO 97/45543 | 12/1997 |
| WO | WO 98/05798 | 2/1998 |
| WO | WO 98/17308 | 4/1998 |
| WO | WO 98/34945 | 8/1998 |

OTHER PUBLICATIONS

Graham Simmons et al., Science 276, Apr. 1997, pp. 276–279, "Potent Inhibition of HIV–1 Infectivity in Macrophages and Lymphocytes by a Novel CCR5 Antagonist".

Christophe Combadiere et al., The Journal of Biological Chemistry 270, Jul. 1995, pp. 16491–16494, "Cloning and Functional Expression of a Human Eosinophil CC Chemokine Receptor".

Manuel A González et al., Biochemical and Biophysical Research Communications 251, pp. 592–596 (1998), "A Hammerhead Ribozyme Targeted to the Human Chemokine Receptor CCR5".

Bartolome Federsppiel et al., Genomics 16, pp. 707–712 (1993), "Molecular Cloning of the cDNA and Chromosomal Localization of the Gene for a Putative Seven–Transmembrane Segment (7–TMS) Receptor Isolated from Human Spleen".

Ritu Goila et al., FEBS Letters 436 (1998) pp. 233–238, "Sequence specific cleavage of the HIV–1 coreceptor CCR5 gene by a hammer–head ribozyme and a DNA–enzyme: inhibition of the coreceptor function by DNA–enzyme".

Nava Sarver et al., Science 247, Mar. 1990, pp. 1222–1225, "Ribozymes as Potential Anti–HIV–1 Therapeutic Agents".

D G Kim et al., Molecular and Cellular Biology 12, 1992, pp. 3636–3643, "Construction of a Bifunctional mRNA in the Mouse by Using the Internal Ribosomal Entry Site of the Encephalomyocarditis Virus".

M Brisson et al., Gene Therapy 6, 1999, pp. 263–270, "A novel T7 RNA polymerase autogene for efficient cytoplasmic expression of target genes".

Larry A Couture et al., TIG 12, Dec. 1996, "Anti–gene therapy: the use of ribozymes to inhibit gene function".

William G Scott et al., TIBS 21, Jun. 1996, pp. 220–224, "Ribozymes: structure and mechanism in RNA catalysis".

John J Rossi et al., Aids Research and Human Retroviruses 8, 1992, pp. 183–189, "Ribozymes as Anti–HIV–1 Therapeutic Agents: Principles, Applications, and Problems".

John M Burke, Nature Biotechnology 15, May 1997, pp. 414–415, "Clearing the way for ribozymes".

Andy Coghlan, New Scientist 152 N° 2059, Dec. 1996, p. 24, "Can gene scissors chop up HIV?".

(Continued)

Primary Examiner—John L. LeGuyader
Assistant Examiner—Jane Zara
(74) Attorney, Agent, or Firm—Nixon & Vanderhye

(57) ABSTRACT

A vector system which can be incorporated in liposomes, comprising at least one DNA vector, the vector or vectors containing a target-cleaving hammerhead ribozymal DNA sequence under control of a promoter effective in human cells and which, upon transcription to RNA will cleave the mRNA transcribed from a target gene encoding the CCR5 or CXCR4 protein.

Preferably the ribozymal DNA contains a first recognition sequence (5' to 3'):
tagattg or ctcact, respectively for CCR5 or CXCR4 and downstream thereof a second recognition sequence acttg or acgttgt respectively for CCR5 or CXCR4.

12 Claims, 18 Drawing Sheets

OTHER PUBLICATIONS

Thomas R Cech et al., Nature 372, Nov. 3, 1994, pp. 39–40, "Hammerhead nailed down".

Scientific American, Sep. 1997, pp. 28–35, "In Search of AIDS–Resistance Genes", Stephen J O'Brien et al.

C Mark Hill et al., Nature 382, Aug. 22, 1996, pp. 668–669, "Natural resistance to HIV?".

Drew Weissman et al., Nature 389, Oct. 30, 1997, pp. 981–985, Macrophage–tropic HIV and SIV envelope proteins induce a signal through the CCR5 chemokine receptor.

Jon Cohen, Science 275, Feb. 28, 1997, pp. 1261–1264, "Exploiting the HIV–Chemokine Nexus".

Alex Eccleston, Nature Biotechnology 15 (8), Aug. 1997, pp. 709, 711, "Chemokine inhibitors for HIV".

Ruth I Connor et al., J Exp. Med., 185 N° 4, Feb. 17, 1997, pp. 621–628, "Change in Coreceptor Use Correlates with Disease Progression in HIV–1 Infected Individuals".

No author stated, Antiviral Agents Bulletin, 10 N° 9, Sep. 1997, pp. 261–262, "Trojan Horse Virus Controls HIV in vitro".

John J Rossi et al., BioDrugs 1, Jan. 1998, pp. 1–10, "Therapeutic Ribozymes: Principles and Applications".

Benjamin J Doranz et al., Cell 85, Jun. 28, 1996, pp. 1149–1158, "A Dual–Tropic Primary HIV–1 Isolate That Uses Fusin and the β–Chemokine Receptors CKR–5, CKR–3 and CKR–2b as Fusion Cofactors".

Bharat M Chowrira et al., Journal of Biological Chemistry, 269 N° 41, Oct. 14, 1994, pp. 25856–25864, "In vitro and in Vivo Comparison of Hammerhead, Hairpin, and Hepatitis Delta Virus Self–processing Ribozyme Cassettes".

No author stated, Nature Biotechnology 16, Jul. 1998, p. 606, "Piggyback ribozymes".

Sun K Jang et al., Journal of Virology 63, Apr. 1989, pp. 1651–1660, "Initiation of Protein Synthesis by Internal Entry of Ribosomes into the 5' Nontranslated Region of Encephalomyocarditis Virus RNA In Vivo".

R Tritz et al., AIDS Weekly Plus, May 19, 1997, p. 31, "Development of Novel anti–CCR5 Hairpin Ribozyme: Treatment for HIV Infections".

Georges Herbein et al., Nature 395, Sep. 1998, pp. 189–194, "Apoptosis of $CD8^+$ Tcells is mediated by macrophages through interaction of HIV gp 120 with chemokine receptor CXCR4".

James, W., Antiviral Chem. and Chemotherapy, vol. 2, No. 4, pp. 191–214.

Milner et al, Nature Biotech., vol. 15, pp. 537–541.

Branch, A., Trends in Bioch. Sci., vol. 23, pp. 45–50.

Friedmann, T., Scientific Amer., Jun. vol., pp. 96–101.

Crystal, R.G. Science, vol. 270, pp. 404–410.

Schofield et al, Brit. Med. Bull., vol. 51, No. 1, pp. 56–71.

Verma et al, Nature, vol. 389, pp. 239–242.

Crooke, S.T. Antisense Research and Application, Chapter 1, pp. 1–50. Publ. by Springer–Verlag.

After 1 hour of Incubation

After 3 Hours of Incubation pCS2 – NLS vector for cloning

↓ Cloning of T7 polymerase gene in the vector

↓ Deleting NLS sequence

RIBOZYMAL NUCLEIC ACID

This application is a continuation of Ser. No. 09/617,505, filed Jul. 14, 2000, now abandoned, and a continuation of International Application PCT/GB99/00134, filed Jan. 15, 1998.

BACKGROUND OF THE INVENTION

1. Field of the Invention

This invention is in the field of recombinant DNA technology and relates to ribozymes.

2. Description of the Related Art

The art is currently exploring the many different ways of attacking the human immunodeficiency viruses (HIV), represented by HIV-1 and HIV-2 or the cellular mechanisms involved in infection by HIV and its progress in vivo. It has recently been shown that (HIV) and simian immunodeficiency virus (SIV) enter target cells by forming a complex between the viral envelope protein and two cell-surface membrane receptors: CD4 and a transmembrane chemokine receptor. Isolates of HIV that differ in cellular tropism use different subsets of chemokine receptors as entry cofactors: macrophage-tropic HIVs primarily use CCR5, whereas dual-tropic isolates use both CCR5 and CXCR4 (also called "Fusin") receptors; CXCR4 is also used by T-tropic viruses.

The role of CCR5 has been reviewed by S. O'Brien and M. Dean, Scientific American, 28–35 (September 1997). That review suggests several ways in which this stage of the HIV infection or maintenance might be blocked. These include:

- obstructing the binding site on CCR5 for HIV by use of chemokine derivative which competes with the natural chemokines or by use of synthetic antibodies,
- vaccination with fragments of CCR5,
- new genes whose products would prevent CCR5 from being made or would stop CCR5 from serving as a docking site for HIV.

PCT Application Publication No. WO 97/45543 proposes to inhibit the action or production of CCR5 receptors in a variety of ways including therapy with antibodies; making variants of CCR5 to use as decoys, thus interfering with the fusion of cells; by way of agents which bind to CCR5 and antisense oligomers and ribozymes to prevent expression of the DNA coding for CCR5.

PCT Application Publication No. WO 97/44055 similarly proposes many ways of inhibiting the action or production of CCR5 receptors, broadening the concept to extend to other chemokine receptors including CXCR4.

In Antiviral Agents Bulletin 10 (No. 9), 261–262 (September 1997), an article "Trojan Horse Virus' Controls HIV in vitro", it is reported that vesicular stomatitis virus (VSV) modified to express CD4 and CXCR4 can selectively target and kill HIV cells in vitro. This approach is described as problematical but "does highlight the potential to use HIV-mimicking attenuated viruses or liposomes with surface cellular HIV receptors for targeted delivery of HIV protease inhibitors, other antiretroviral drugs, antisense agents, gene therapies, ribozymes or other agents to HIV-infected cells."

SUMMARY OF THE INVENTION

It has now been found that mRNA coding for the CCR5 and CXCR4 proteins can be cleaved by hammerhead ribozymes so effectively as to block production of these proteins.

In one aspect, the invention provides a vector system comprising at least one DNA vector, the vector or vectors containing a target-cleaving hammerhead ribozymal DNA sequence under control of a promoter effective in human cells and which, upon transcription to RNA will cleave the mRNA transcribed from a target gene encoding the CCR5 or CXCR4 protein.

The linkage of the ribozymal DNA sequence to the promoter can be direct, and need employ only a single vector. However, there are advantages in an indirect linkage which amplifies the effect of the promoter. Such an indirect linkage will normally require two or more vectors. Thus, the invention includes a vector system comprising at least two DNA vectors, wherein a first vector contains a first promoter effective in human cells, operably linked to a gene which is expressible to produce an activator protein capable of acting on a second promoter, and a second vector contains the second promoter operably linked to the target-cleaving hammerhead ribozymal DNA sequence referred to above. The ribozymal DNA sequence can comprise a single sequence for cleaving the CCR5 or CXCR4 RNA or sequences for cleaving both CCR5 and CXCR4 RNA. The term "vector system" as used herein is generic terminology encompassing a single vector or a kit or composition or two or more vectors.

Strictly, a ribozyme is an RNA molecule which cleaves an RNA target. Some of the literature is using the term to describe DNA molecules which are transcribed to RNA, thus generating the ribozyme proper. In this specification, the term "ribozymal DNA" means DNA transcribable to the ribozyme proper.

The invention includes liposomes containing a DNA vector system as defined above and pharmaceutical compositions comprising the liposomes.

Still further, the invention includes the vector, composition and liposomes, as described above, for use in treating diseases associated with infections, especially HIV and AIDS. It includes also use of the nucleic acid, vector, or liposomes in the preparation of a medical formulation for such a purpose. Further, where patent law permits (e.g. Australia, USA) it includes a method of treating a patient suffering from a HIV-infection, which comprises administering to the patient the vector, composition or liposomes in an effective dose or as part of an effective dose when administered in conjunction with another treatment.

Further, the invention includes ribozymal DNA, both per se and as a ribozymal DNA sequence contained within a vector, the ribozymal DNA further comprising, downstream of the target-cleaving ribozymal sequence, a 3'-autocatalytic hammerhead ribozymal DNA sequence, so that when the ribozymal DNA is transcribed to RNA it has a form representable as a double hammerhead, having first and second stems of a target-cleaving ribozyme which targets CCR5 or CXCR4 mRNA and first and second stems of 3'-autocatalytic ribozyme, together with a common, third stem joining the two hammerheads. This third stem is preferably of at least 4 bases near the 3' end of the CCR5 or CXCR4 ribozyme sequence, capable of base-pairing with a complementary sequence of at least four bases near the 3' end of the autocatalytic ribozyme sequence, so as to form, when base-paired, the said common stem joining the hammerheads of the target-cleaving and 3'-autocatalytic ribozymes.

The verb "to comprise", whenever used herein in any grammatical form, means to consist of or include.

ADDITIONAL PRIOR ART

AIDS Weekly Plus May 19, 1997, page 31, contains a report of an Abstract by R. Tritz et al. submitted to the "Keystone Symposia on Molecular and Cellular Biology entitled "Discovery and Development of Novel Therapeutic Agents for the 21$^{st}$ Century", Mar. 16–21, 1997, Tamarron, Colo., USA. This abstract proposes that CCR5 is a suitable target for ribozyme gene therapy and reports that a number of hairpin ribozymes that target CCR5 RNA have been made.

DESCRIPTION OF THE PREFERRED EMBODIMENTS

The ribozymes in this invention are of the hammerhead type. Ribozymes have catalytic sequences which cleave the RNA at the desired target site. The catalytic sequences of hammerhead ribozymes are usually of the form (5' to 3')(1) cuganga . . . and (2) . . . gaa, where n is any nucleotide. In the present invention n is preferably u. They are separated by a stabilising structure, which is preferably a stem loop. The ribozymal DNA in the invention can have this form (substituting thymine for uracil).

The most preferred target sequences, for the purposes of the present invention, are CCR5: 5' caa<u>guc</u>caaucua 3' (SEQ ID NO: 1)

CXCR4: 5' acaac<u>guc</u>agugag 3' (SEQ ID NO: 2)

The underlined portion is the essential sequence of three bases required by the hammerhead ribozyme used in the present invention.

Immediately upstream and downstream of the catalytic sequences lie target-binding (i.e. target-recognition) sequences. The target is RNA, and the ribozyme which is RNA, is complementary to the target RNA, (disregarding the additional c nucleotide present in the target, as explained below).

The sequences involved in the preferred target and in the preferred ribozyme binding thereto may therefore be summarised as follows:

```
CCR5                                                      (SEQ ID NO: 1)

(a) 5' Caagu               c*         caaucua 3'  (target RNA)

(b) 3' guuca -cat.seq.-s.l. -cat seq. -guuagau 5'  (rz RNA)

(c) 5' caagt -cat.seq.-s.l. -cat seq. -caatcta 3'  (rz DNA; strand 1)

(d) 3' gttca -cat.seq.-s.l  -cat seq. -gttagat 5'  (rz DNA; strand 2)

CXC R4                                                    (SEQ ID NO: 2)

(a) 5' acaacgu            c*          agugag 3'  (target RNA)
```

```
(b) 3' uguugca-cat.seq.-s.l. -cat.seq.-ucacuc  5' (rz RNA)

(c) 5' acaacgt-cat.seq.-s.l. -cat.seq.-agtgag  3' (rz DNA; strand 1)

(d) 3' tgttgca-cat.seq.-s.l. -cat.seq.-tcactc  5' (rz DNA; strand 2)
```

(*= cleaved nucleotide,
cat.seq.= catalytic site;
s.l.= stem loop)

Figure 4A:
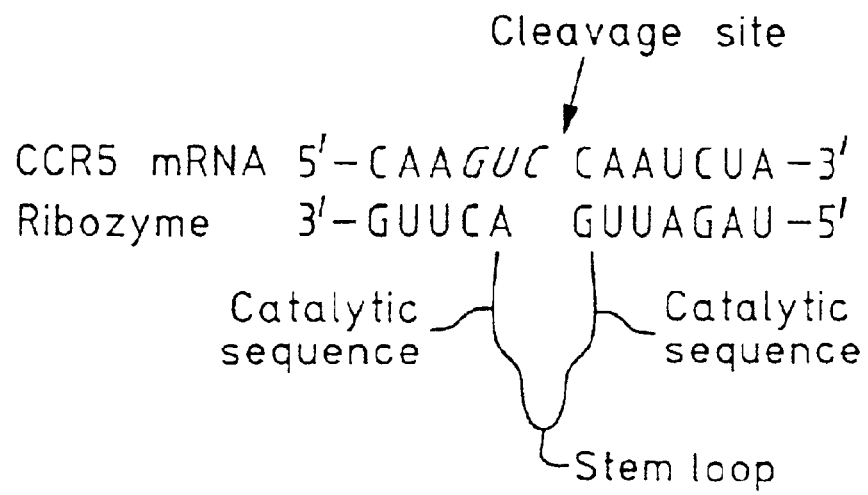
FIGS. 4a (SEQ ID NO: 1) and 4b (SEQ ID NO: 2) are schematic drawings of target-cleaving ribozyme sequences used in this invention, in relation to CCR5 and CXCR4 mRNA targets.
Figure 4B:
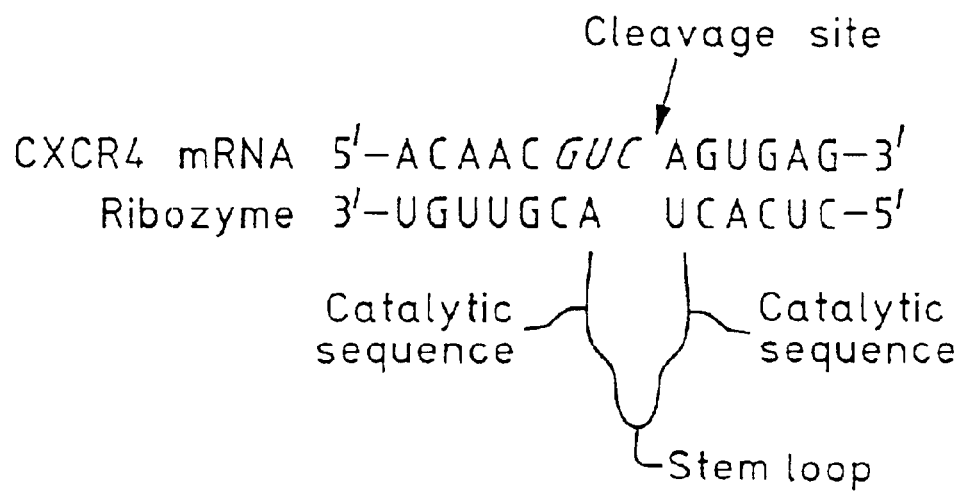

For the ribozyme targeting the CCR5 mRNA, 5' uagauug 3' is the first target-recognition sequence and 5' acuug 3' is the second target-recognition sequence. The cleavage site in the target is guc*, the asterisked c nucleotide being the cleavage site and therefore having no counterpart in the ribozyme. Sequences (a) and (b) for CCR5 are shown in FIG. 4 of the drawings. For the ribozyme targeting the CXCR4 mRNA 5' cucacu 3' and 5' acguugu 3' are the first and second target-recognition sequences. The cleavage site in the target is again guc*. A preferred sub-genus of ribozyme for use in the invention is those which have these target recognition sequences.

In the following description, the structure of hammerhead ribozymes is discussed in RNA terms, but it will be understood that the ribozymal DNA, from which they are transcribed, corresponds, substituting thymine for uracil. It will also be appreciated that the conformations of these ribozymes shown herein are those evident from base-pairing and other energetic considerations and that the invention is in no way limited by these drawings, i.e. that the invention includes other conformations of the same molecules.

Hammerhead ribozymes are maintained by two stem loops, a first stem loop ("stem I") preceding the first target-recognition sequence and the second stem loop ("stem II") lying between the first and second target-recognition sequences. These two stem loops may have any desired form, but typically comprise 3 to 5 complementary base pairs forming the stem and 4 or 5 bases in the loop. FIG. 1, relating to a ribozyme which targets the CCR5 mRNA, illustrates 4 base pairs in the stem portion proper and 5 bases in the loop portion. FIG. 11, relating to a ribozyme which targets the CXCR4 mRNA, illustrates 5 base pairs in stem I, 4 in stem II and 4 base pairs in each loop portion.

Following the second catalytic sequence is a third stem, which consists of or includes the second target-recognition sequence. In one embodiment of the invention, stem III has a special sequence of guc at the 3' end which can be added in part or in full, if not naturally present. Where, as here, g is the natural ending, uc is added as an over-hang, see FIG. 1, so that the last few bases thereof pair with the bases of the second catalytic sequence. In FIG. 1, this is achieved by a-u and g-c base pairs. This type of construction is suitable when the ribozyme does not contain a 3'-autocatalytic sequence but can also be used when it does.

More preferably, the ribozyme contains a 3'-autocatalytic sequence. Such sequences are known per se, especially from PCT Patent Application N$^o$ WO 97/17433 (Medical University of South Carolina). The 3'-autocatalytic sequence is preferably designed so that a sequence near the 3' end of the target-cleaving ribozyme is base-paired with a downstream part of the autocatalytic sequence at or close to the 3-end thereof. These preferred constructs have at least 4 base pairs in stem III, i.e. 4 from the target-cleaving ribozyme which are base-paired with 4 from the autocatalytic ribozyme. They may have as many as 10 of these base pairs. Typically the over-hang of non-base-paired nucleotides extending beyond stem III is only 1 or 2 at the 3'-end of the target cleaving ribozyme sequence and 0 to 5 at the 3'-end of the autocatalytic sequence. Such constructions are exemplified for CCR5 in FIG. 2 and for CXCR4 in FIG. 11. Here, the 3'-autocatalytic (=self-cleaving) sequence is in the form of a hammerhead ribozyme comprising a 3'-cleavage site (guc), a first stem loop ("scas Stem I"), a second stem loop ("scas Stem II") and a third stem ("scas Stem III"), the third stem being base-paired with Stem III of the target-cleaving ribozyme. Cleavage occurs after the c of the guc 3'-cleavage site. The catalytic sequence (cugauga) between scas stem I and scas stem II is one which assists in stabilising the hammerhead structure and is also used in WO 97/17433. Between Stems II and III there is provided a gaa catalytic site.

The ribozymes used in the present invention may contain a 5'-autocatalytic sequence, for example as described in WO 97/17433. In WO 97/17433 a double ribozyme is provided containing a centrally located BglII cloning site agatct into which any desired target-recognition and catalytic sequences can be inserted. In WO 97/17433, the insert is of 42 bases. These consist of first target-recognition sequence (8 bases), catalytic and structure-stabilising sequences (23 bases) and a second target-recognition sequence (11 bases, the last two of which are the ag of a BglII site). With minor modifications, the same construction could be adapted to the present invention, e.g. substituting the DNA equivalent of 36 bases, 13–48 of FIG. 1, for the 23 bases of WO 97/17433, adding nucleotides necessary for cloning into a BglII site at the 3'-end thereof. In this construction Stem I would be dispensed with and replaced by the 5'-sequence of WO 97/17433 including the 5'-autocatalytic site. However, in WO 97/17433 the portion of sequence between the catalytic sites is not in a tight stem loop form and so appears less structure-stabilising.

The construct in the present invention is one or more vectors containing ribozymal DNA. To be effective in eukaryotic, especially human cells, the ribozymal DNA should be directly or indirectly controlled by a eukaryotic cell promoter. One especially such suitable promoter is the cytomegalovirus promoter. It is also preferable to provide other sources of RNA polymerase for transcription of the RNA, rather than rely wholly on endogenous polymerase in the cells in the body which are to be transfected. Preferably the polymerase is one which catalyses the action of the promoter, typically by acting on it in trans. That is to say, a first DNA molecule or length of DNA is expressed to produce a polymerase which acts on the promoter, contained in another DNA molecule or distinct length of DNA, which promotes transcription of the ribozymal DNA. Conveniently, DNA coding for the polymerase is provided within the vector, downstream of the ribozymal DNA. The polymerase produced by the DNA will then act in cis, since it will "feed back" to stimulate its own the promoter. See e.g. FIG. 17, plasmid 2 or the autopolymerase vector in FIG. 18.

Figure 17:
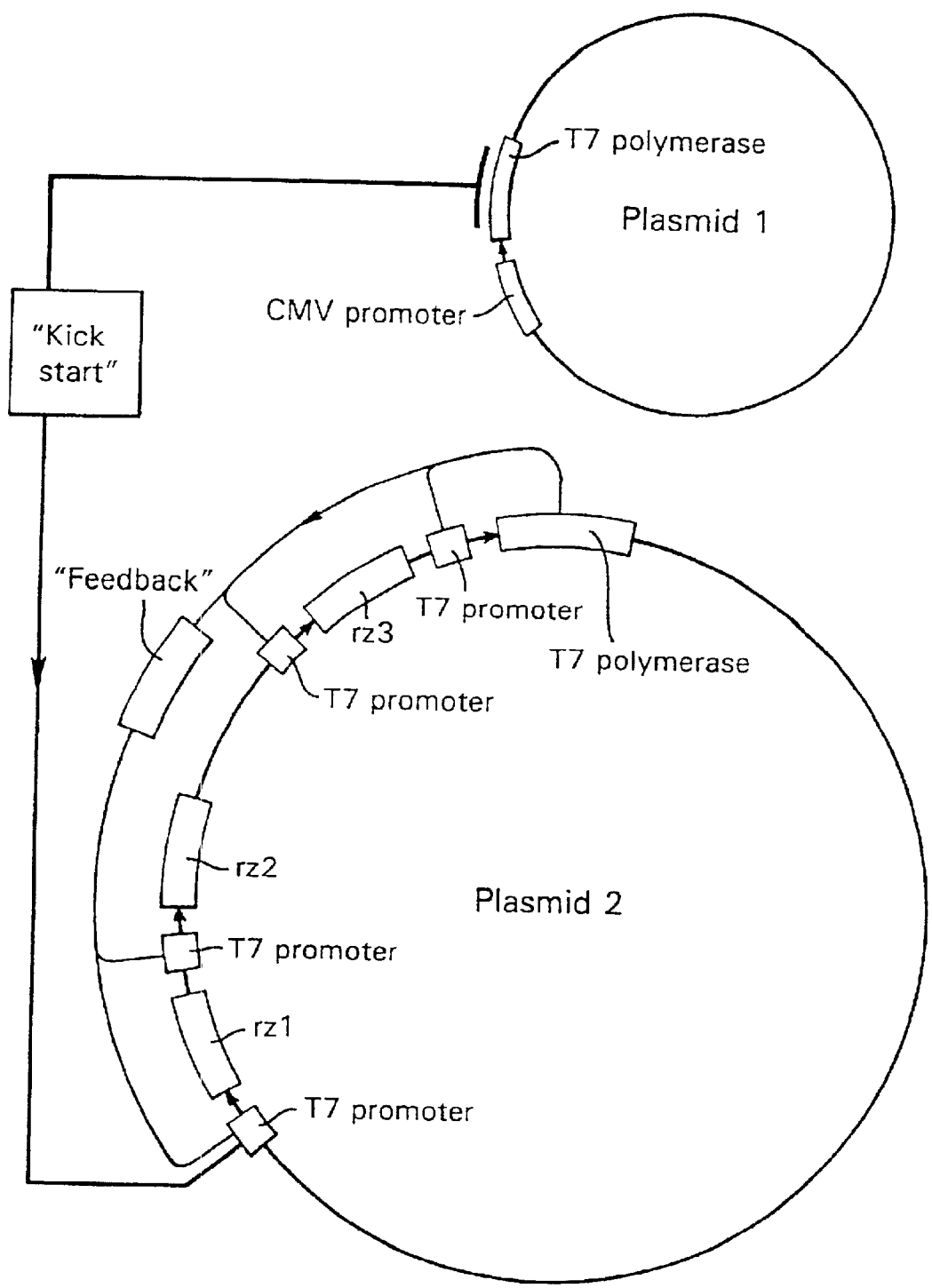
FIG. 17 is a schematic diagram of a 2-plasmid vector system of the invention, the first comprising a CMV-promoter driving a transcription of RNA from a T7 polymerase gene and the second comprising T7 promoter driving transcription of RNA from three ribozymal DNAs in tandem.

Referring to FIG. 17, the plasmid 2 comprises a ribozymal DNA "rz1" which cleaves CCR5 or CXCR4 RNA or both. However, it has long been thought desirable to attack the HIV at more than one point in its cycle of infection, growth and replication. Thus, the same vector could contain one or more other kinds of ribozymal DNA which will target other RNA produced by HIV or required to make a protein on which HIV depends for its growth or replication. Thus, FIG. 17 illustrates three kinds of ribozymal DNA as rz1, rz2 and rz3. Any one of these may be against CCR5 or CXCR4 RNA or both, while the other could be absent or could target another RNA produced by HIV or by a chemokine receptor. Especially preferred are ribozyme sequences targeting the mRNA of chemokine receptors CCR2b or CCR3. The RNA/DNA sequence of CXCR4 is disclosed in B. Federsppiel et al., Genomics 16, 707–712 (1993). The RNA/DNA sequences of CCR2b and CCR3 are also known, enabling ribozymes targetting these chemokine receptors to be developed, preferably analogously to those for CCR5 and CXCR4. For CCR2b, which was previously called human monocyte chemoattractant protein 1 receptor (MCP-1RB) see GenBank, Accession No. U03905 and I. F. Charo et al., Proc. Natl. Acad. Sci. USA 91, 2752–2756 (1994) and for CCR3 see GenBank, Accession No. U28694 and C. Combadiere et al., J. Biol. Chem. 270, 16491–16494 and 30235 (1995) and ibid., 271, 11034 (1996). The role of CCR2b and CCR3 in HIV infections is described by B. J. Doranz, Cell 85, 1149–1158 (1996) and by R. I. Connor. J. Exp. Med. 185, 621–628 (1997).

Another target is a sequence at the 3'-end of the HIV viral mRNA (a 5' leader sequence in DNA terms). See PCT Application Publication N° WO 97/07667 (University of California), which describes a hairpin ribozyme and identifies the target.

In order to "kick start" the promoter it is desirable to provide a separate source of the polymerase, either as the enzyme itself or, more preferably in the form of another vector, which is also preferably a plasmid, dedicated for this purpose. See FIG. 17, plasmid 1 and FIG. 18.

Figure 18:
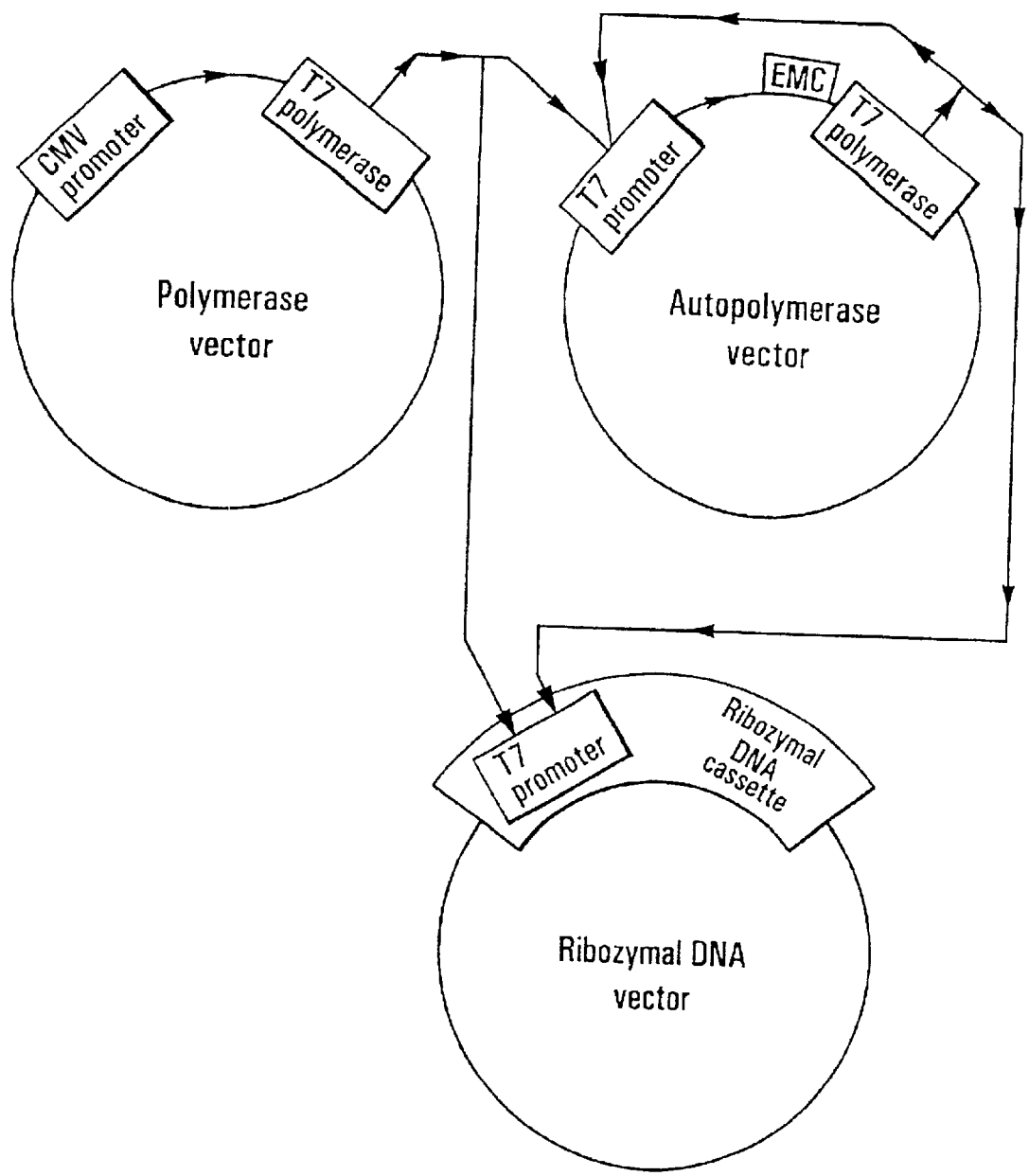
FIG. 18 is a schematic diagram showing a 3-plasmid vector system of the invention, the first plasmid comprising a CMV promoter driving transcription of mRNA from a T7 polymerase gene, the second plasmid comprising a T7 promoter driving transcription of mRNA from a T7 polymerase gene and the third plasmid comprising a T7 promoter driving transcription of RNA from a ribozymal DNA which targets CCR5 or CXCR4 RNA or both.

Referring to FIG. 18, a first plasmid contains the CMV promoter driving transcription of the T7 polymerase gene, a second plasmid contains the T7 promoter and a translational enhancer (exemplified as an IRES and illustrated as from EMC virus) for the production of T7 polymerase and a third plasmid in which a T7 promoter, activated by the polymerase produced by the first two plasmids, drives transcription of the CCR5 and/or CXCR4 ribozymes. Other translational enhancers could be used in place of that shown.

Other targets are the LTR (long terminal repeat) and tat gene regions of HIV. Hammerhead ribozymes for this purpose are described in PCT Publication WO 95/04818, which also contains a bibliography of other HIV genes previously targeted, including the gag gene [Chang et al., Clinical Biotechnology 2, 23 (1990) and N. Sarver et al., Science 247, 1222–1225 (1990) and the vif gene [E. U. Lorentzen et al., Virus Genes 5, 17–23 (1991)].

In order to increase efficiency, the promoter can be inserted in front of each ribozyme sequence as well as the polymerase sequence, as shown in FIG. 17. However, this arrangement can be varied by using a single promoter, altering the order of the genes. Also, by using several vectors in place of plasmid 2, expression of the ribozymes can be varied.

Methods of delivery that may be used include encapsulation in drug delivery vehicles, especially, liposomes, transduction by retroviral vectors, and conjugation with cholesterol.

Drug delivery vehicles are effective for both systematic and topical administration. They can be designed to serve as a slow release reservoir, or to deliver their contents directly to the target cell. Some examples of such specialized drug delivery vehicles are liposomes, hydrogels, cyclodextrins, biodegradable nanocapsules, and bioadhesive microspheres.

Liposomes are preferred. They are hollow spherical vesicles composed of lipids arranged in a similar fashion as the lipids of the cell membrane. They have an internal aqueous space for entrapping water soluble compounds and range in size from 0.05 to several microns in diameter. Liposomes can deliver the DNA to cells, so that the nucleic acid remains biologically active.

They can easily be prepared by mixing the DNA with a liposome-forming lipid such as a dialkyl or diacylglycerol or phosphatidinylcholine, as known in the art of liposome formation. See J. J. Rossi et al. AIDS Research and Human Retroviruses 8, 183–189 (1992).

Liposome preparations useful in the invention comprise: (a) lipofectamine reagent (GIBCO BRL, Gaithersburg, Md. USA) containing a polycationic lipid molar ratio, (b) the cationic lipid, DDAB and DOPE, in a 2:1 ratio, R. Philip, Mol. Cell. Biol. 14, 2411–2418, (1994); and (c) DMRIE, optionally in combination with DOPE, e.g. in a 1:1 molar ratio (VICAL Corp. San Diego, Calif., USA). Newer liposomes, for example the serum-resistant cationic lipid GS 2888, J. G. Lewis et al., Proc. Natl. Acad. Sci. USA 93, 3176 (1996) and liposomes containing a polylysine/DNA complex, S. Li and L. Huang, J. Liposome Research 7, 63–75 (1997), can also be used.

Nanoparticles and hydrogel carriers have been developed for chemotherapeutic agents and protein-based pharmaceuticals, and consequently, can be adapted for ribozyme delivery for the purposes of the present invention.

Another delivery method is via T-cells. Compatible T-cells, preferably the patient's own are infected with ribozymal DNA of the invention, for example by electroporation and the patient is then infused with these cells. Electroporation of T-lymphocytes with DNA is described in Example 6 of PCT Publication WO 96/22638 (Gene Shears Pty Ltd.) and this method can be applied in the present invention.

The compositions for pharmaceutical use will normally contain a magnesium salt, preferably as buffered magnesium chloride, this being required for the function of the ribozyme. They may also contain a carrier or diluent, which can include a suspending or emulsifying agent.

Vector systems of the invention, preferably in a liposome formulation, are preferably systemically administered, e.g. by an intravenous, subcutaneous, intraperitoneal, intranasal or intrathecal route. The dosage of ribozyme provided by the vector system will depend upon the disease indication and the route of administration but should be up to 200 mg/kg and usually at least 10 mg/kg of body weight/day. The number of doses will depend upon disease delivery vehicle and efficacy data from clinical trials.

The following Examples illustrate the invention.

EXAMPLES

1. CCR5 DNA Cloning and Expression

Human CCR5 mRNA was isolated from the blood sample of a normal individual as follows. Human peripheral blood mononuclear cells (PBMC) were cultured as described in "Methods of Immunological Analysis", R. F. Masseyeff, W. H. Albert and N. A. Staines, pub. V.C.H. Verlag, Weinheim Germany (1993), Vol. 3 "Cells and Tissues", pp. 121–135 and isolated using gradient centrifugation. The cells were then stimulated with red kidney bean lectin (PHA-L, Sigma) at 1 ug/ml for 24 hours. The stimulated cells were treated with 4M guanidinium thiocyanate and SDS solution and then subjected to acid-phenol separation and isopropanol precipitation procedures, all in accordance with the procedure described in "Molecular Cloning: A Laboratory Manual", ed. J. Sambrook, E. F. Fritsch and J. Maniatis, Cold Spring Harbor Laboratory Press, Cold Spring Harbor, 2nd ed. 1989. cDNA was then made with oligo dT (16–18 bases) and reverse transcriptase by a standard procedure. PCR was performed with the primers designed on the basis of the DNA sequence disclosed in M. Samson et al., Biochemistry 35, 3362–3367 (1996). Thus, the sequence of the forward primer was 5'-tgcacagggt ggaacaagat gg-3' (SEQ ID NO: 3)

and the sequence of the reverse primer is

5'-cacttgagtc cgtgtcacaa gc-3' (SEQ ID NO: 4)

Figure 7:
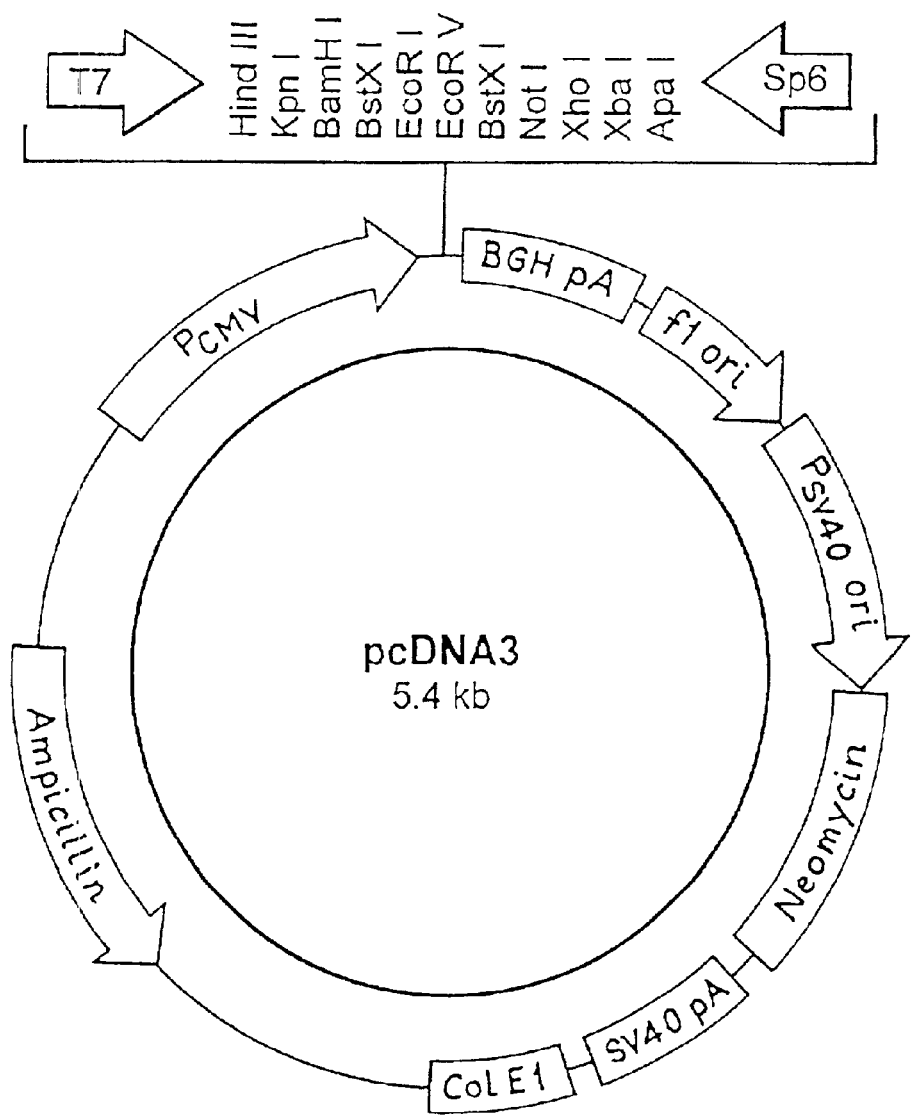
FIG. 7 is a map of plasmid pcDNA3 used in cloning CCR5 cDNA.

Taq polymerase was used, which gave an a (adenosine) overhang ending to the 3'-end. The PCR product was then cloned into pcDNA3, a 5.4 Kb plasmid sold by Invitrogen UK Ltd, (see FIG. 7) in a EcoRV restriction site. Then, t (thymidine) nucleotides were added to the 3'-ends of an EcoRV restriction site of the vector, so as to produce a "ta cloning" site in the vector. "ta cloning" is described by J. M. Clark, Nucleic Acids Research 16, 9677–9686 (1988), in U.S. Pat. No. 5,487,993 and on the Worldwide Web at http://wvw.gene-labs.com/pro42.htm. The plasmid was then transfected into E. coli XL1-blue and screened. The CCR5 DNA insert was completely sequenced and found to be identical to the published CCR5 DNA sequence. As shown in FIG. 7, pcDNA3 contains a T7 promoter before the multiple cloning site. CCR5 mRNA transcripts were produced by adding T7 polymerase in "Ribomax", solution as described by the "Protocols and Applications Guide" of Promega Ltd.

2. CCR5 Ribozymal DNA Cassette

Figure 3:
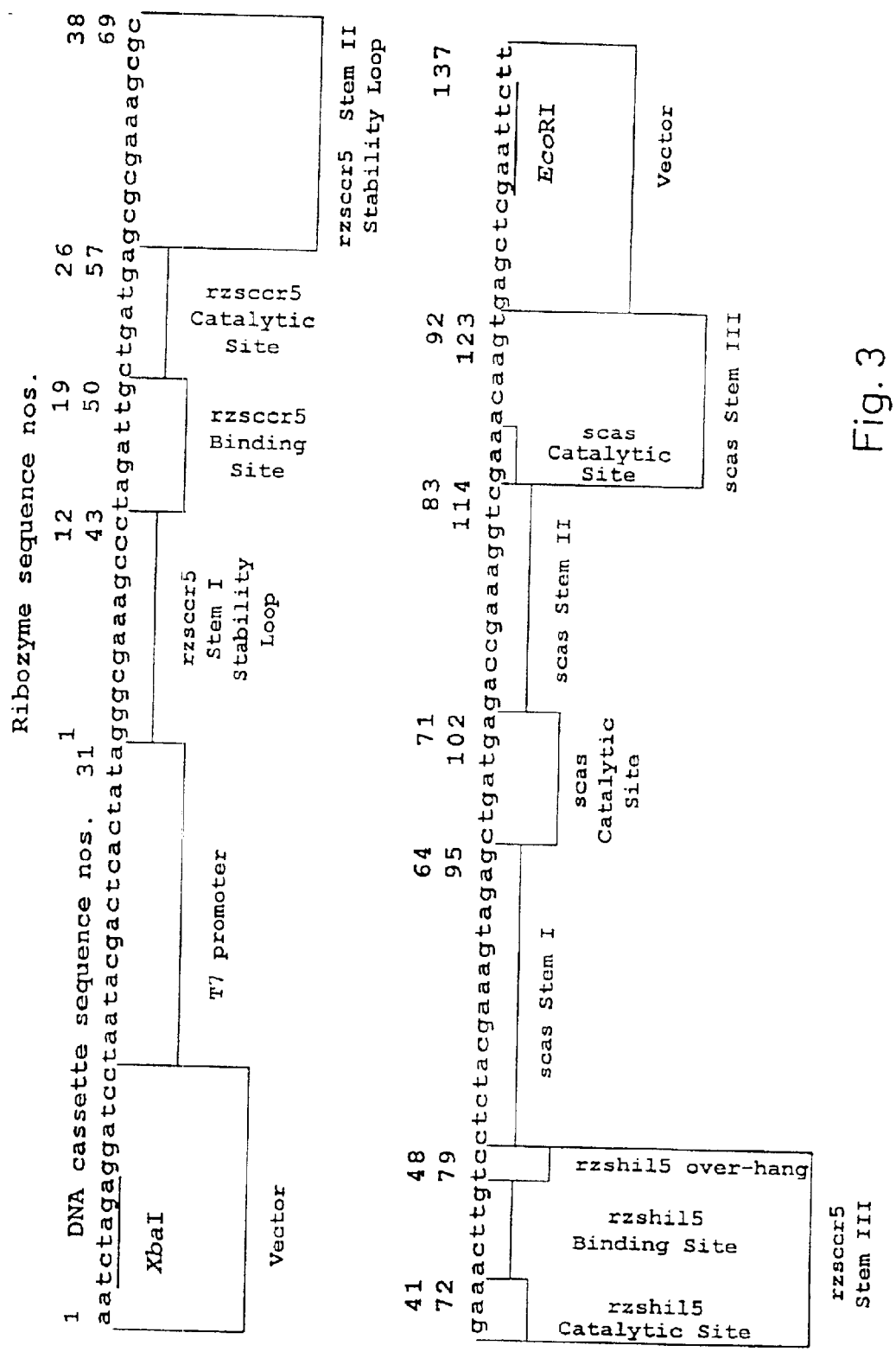
FIGS. 3 (SEQ ID NO: 5) and 12 (SEQ ID NO: 8) show the DNA sequences of cassettes comprising the ribozymal DNA of FIGS. 2 and 11 driven by a T7 promoter.

A complete ribozymal DNA cassette was constructed having the nucleotide sequence SEQ ID NO:5, described more fully in FIG. 3:

```
aatctagagg    atcctaatac    gactcactat
agggcgaaag    ccctagattg    ctgatgagcg
cgaaagcgcg    aaacttgtcc    tctacgaaag
tagagctgat    gagaccgaaa    ggtcgaaaca
agtgagctcg    aattctt       137
```

It was made from a forward oligomer from positions 1 to 80 of the coding sequence and a reverse one from positions 137 to 56, using an oligonucleotide synthesizer. 25 bases at the 3'-ends of the oligomers were totally complementary to each other and the two strands were annealed. Their elongation to become a complete double strand was carried out with DNA polymerase on a PCR machine. The 137-long ds DNA cassette was cloned into pUC19 using XbaI and EcoRI sites (see FIG. 3) for the 5'-end and 3'-end respectively. Its sequence was confirmed by DNA sequencing. The cassette contains a T7 promoter, as the commercially available pUC19 does not contain this site.

Figure 1:
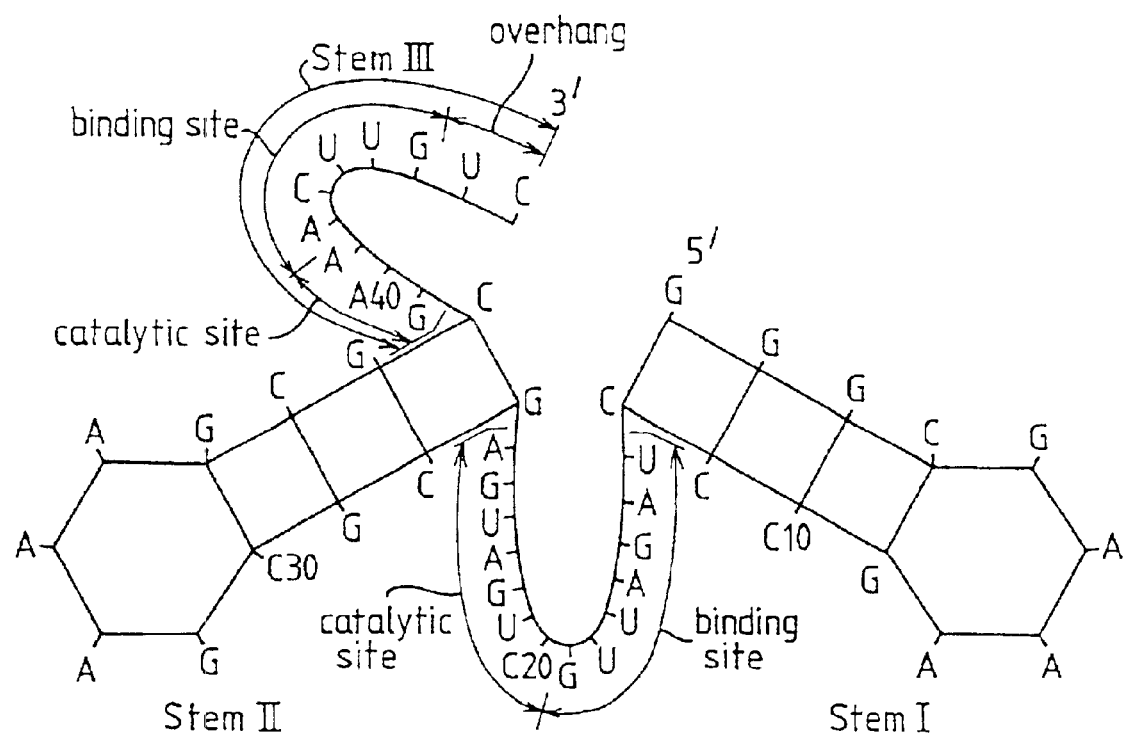
FIG. 1 is a schematic drawing of a target-cleaving ribozyme sequence (SEQ ID NO: 13) of the invention for CCR5.
Figure 2:
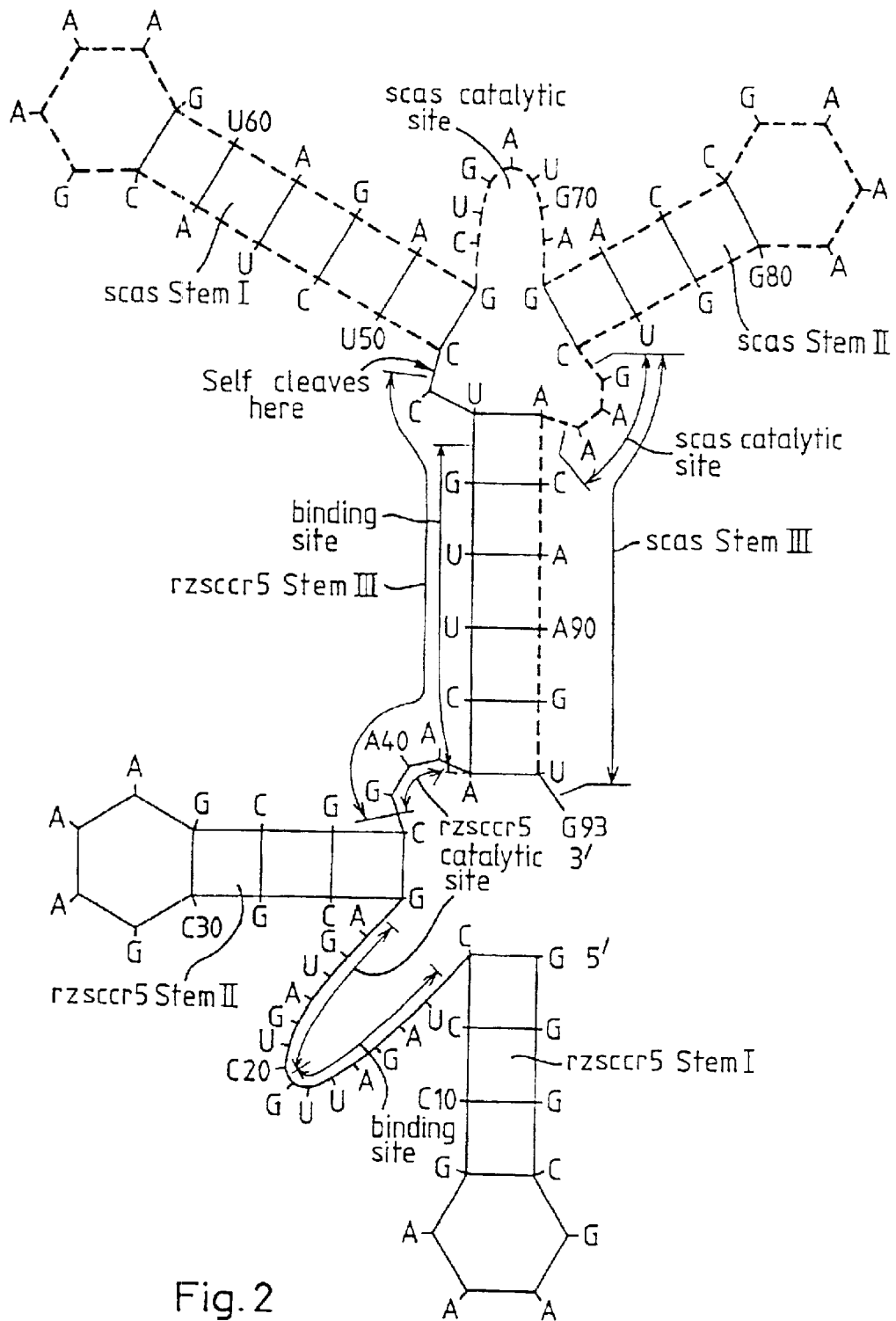
FIGS. 2 (SEQ ID NO: 14) and 11 (SEQ ID NO: 15) are schematic drawings of target-cleaving ribozymal DNA sequences linked to a 3'-autocatalytic sequence to provide a double hammerhead ribozymal DNA for targetting CCR5 and CXCR4 mRNA, respectively.

Referring to FIGS. 3 and 1, the cassette comprises in order (5' to 3'):

| FIG. 3 Base Nos. | FIG. 1 Base Nos. | Function |
|---|---|---|
| 1–14 | | Vector sequence. |
| 15–31 | | T7 promoter. |
| 32–43 | 1–12 | First structure-stabilising stem loop of the target-cleaving ribozymal DNA ("rzsccr5 stem I"). |
| 44–50 | 13–19 | First target-recognition sequence (binding site). |
| 51–57 | 20–26 | First catalytic sequence of the target-cleaving ribozymal DNA. |
| 58–69 | 27–38 | Second structure-stabilising stem loop of the target-cleaving ribozymal DNA ("rzsccr5 stem II"). |
| 70–72 | 39–41 | Second catalytic sequence of the target-cleaving ribozymal DNA (gaa), forming part of stem III ("rzsccr5 stem III") |
| 73–79 | 42–48 | Second target-recognition sequence, ending in g with uc overhang, forming the remainder of rzsccr5 stem III. |
| 80–95 | | First structure-stabilising stem loop of autocatalytic ribozymal DNA ("scas stem I"). |
| 96–102 | | First scas catalytic site. |
| 103–114 | | Second structure-stabilising stem loop of autocatalytic ribozymal DNA ("scas stem II"). |
| 115–123 | | Bases gaa forming the second scas catalytic site, followed by a 6-base sequence which base-pairs with 6 complementary bases of the second target-recognition sequence above, thus forming another stem ("scas stem III"). |
| 124–137 | | Vector sequence (includes g overhang as nt 124). |

The ribozymal RNA was made by adding T7 polymerase in "Ribomax" solution, as described by Promega's "Protocols and Applications Guide" manual. "Ribomax" is a balanced salt solution containing the necessary magnesium ions for ribozymal activity. T7 polymerase triggers the T7 promoter to transcribe RNA from the DNA. Transcripts were isolated by using RNase-free DNase, followed by acid/phenol isolation of RNA, then ethanol precipitation. It was done as described in "Molecular Cloning—A Laboratory Manual", cited above.

When the RNA was run on an agarose gel, the ribozyme before cleavage (103 bases) was clearly separated from the ribozyme after cleavage (48 bases, FIG. 1). RNA was shown by ethidium bromide contained in the gel (visualised under UV light).

3. Human CCR5 Target Cleavage

Human CCR5 DNA prepared as described in Section 1 above, cloned into pcDNA3, was transfected into E. coli XL1Blue ("Molecular Cloning—A Laboratory Manual", cited above) to produce anRNA transcript of CCR5.

Figure 5A:
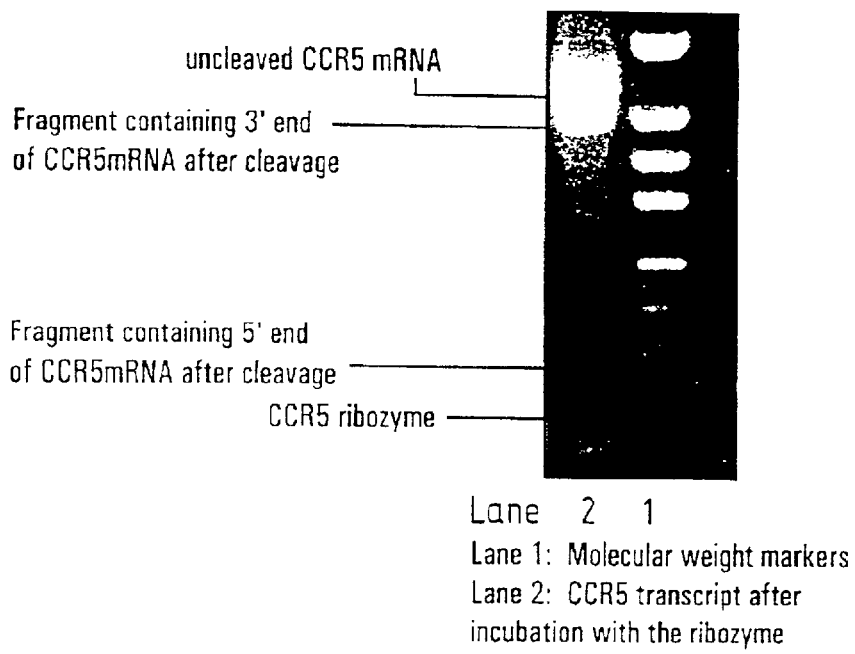
FIGS. 5a and 5b are photographs of agarose gels with ethidium bromide, containing human CCR5 mRNA and incubated with a ribozyme corresponding to the ribozymal DNA sequence provided by a vector system of the invention; these photographs shows how the CCR5 RNA has been cleaved after 1 hour of incubation (FIG. 5a) and after 3 hours of incubation (FIG. 5b)
Figure 5B:
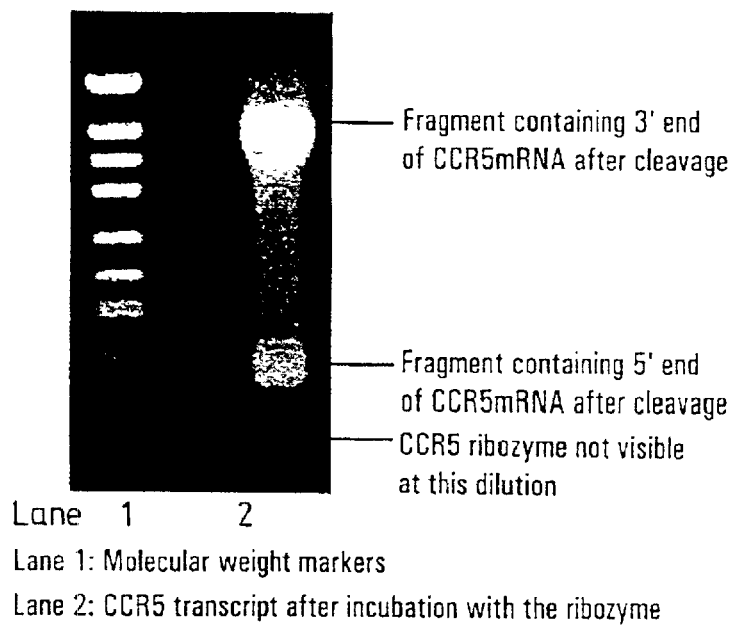

Ribozymes transcribed from the plasmid described in Section 2 above were incubated with the CCR5 RNA transcript at a molar ratio of 1 mole ribozyme to 10 moles of CCR5 RNA transcript. Within 3 hours of incubation at 37° C., total cleavage of the CCR5 mRNA target was achieved. The RNA was run on 2% agarose gel containing ethidium bromide. Gel photographs taken under UV irradiation are presented in FIGS. 5a and 5b. FIG. 5a, left-hand lane, shows the products after 1 hour of incubation, when the CCR5 mRNA was not completely cleaved and so appeared as a band of high molecular weight at the top. The right-hand lane consists of molecular weight markers. Also present in the left-hand lane were bands of lower molecular weight, attributable (in descending order of molecular weight) to a 3'-fragment of the CCR5 mRNA after cleavage, a 5'-fragment of the CCR5 mRNA after cleavage and the ribozymal RNA. Thus it is clear that the rzsccr5 ribozyme can self-cleave to produce an active ribozyme that cleaves CCR5 catalytically. Referring to FIG. 5b, the right-hand lane shows the products after 3 hours of incubation, when the CCR5 mRNA has been completely cleaved. The band representing uncleaved mRNA in FIG. 5a has disappeared and has been replaced by a band corresponding to the 3'-end of the cleaved product, at lower molecular weight. The fragment containing the 5'-end of the CCR5 mRNA is visible at even lower molecular weight than in FIG. 5a. There is no visible band containing CCR5 ribozyme. This is because the gel was loaded with a sample ten times more dilute than that used in FIG. 5a.

4. Transfection of Plasmids into PBMC

Plasmids were transfected into normal human peripheral blood mononuclear cells (PBMC) obtained from a blood bank. The cells were isolated, stimulated with PHA-L and IL-2 using the standard procedure of S. J. Martin et al., J. Immunol. 152, 330–342 (1994). Six days later the cells were treated by a procedure adapted from that of Gibco Life Technologies Ltd., as follows. 12 µl of DMRIE-C (Life Technology Ltd.), a liposome-forming preparation, were mixed with 0.5 ml of OPTI-MEM I reduced serum medium. 20 µl or 200 µl of plasmids were added in 0.5 ml of OPTI-MEM I medium to the mixture and mixed well with it. The solution was then left at room temperature for 45 minutes before 0.2 ml of PBMC suspension containing 4 million cells was added. The cellular suspension was prepared with ¼ culture supernatant and ¾ RPMI, topping up with IL-2 to 10 U/ml. The final mixture was incubated at 37° C. for 4–5 hours with 5% $CO_2$. Then, the cells were resuspended in normal culture medium (RPMI1640, IL-2 10 u/ml and 10% Foetal Calf Serum) by adding the mixture in aliquots to the medium. The viability at this point was more than 90% by Trypan Blue staining. The cells were then cultured in the normal way for analysis.

Figure 6A:
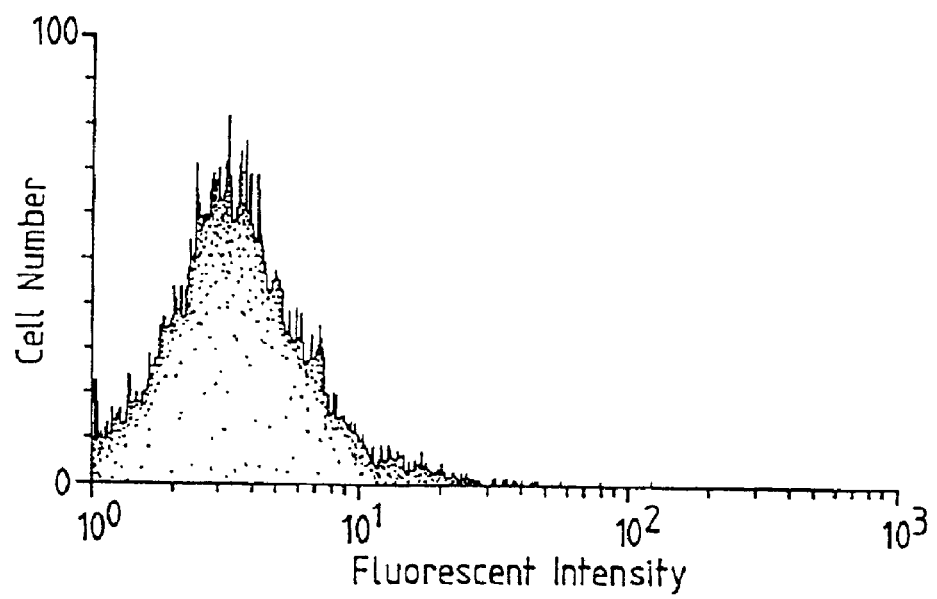
FIGS. 6a and 6b, 15a and 15b and 16a and 16b are plots of cell number (y-axis) against fluorescent intensity (x-axis) of cells untransfected (6a, 15a, 16b) and transfected (6b, 15b, 16b) with a liposome preparation containing a plasmid expressing a reporter gene encoding β-galactosidase (6b) or a plasmid vector system of the invention containing a ribozyme targeting CCR5 mRNA (15b) or CXCR4 mRNA (16b): the fluorescent intensity indicates the level of β-galactosidase (6a, 6b), CCR5 protein expression (15a, 15b) and CXCR4 protein expression (16a, 16b)
Figure 6B:
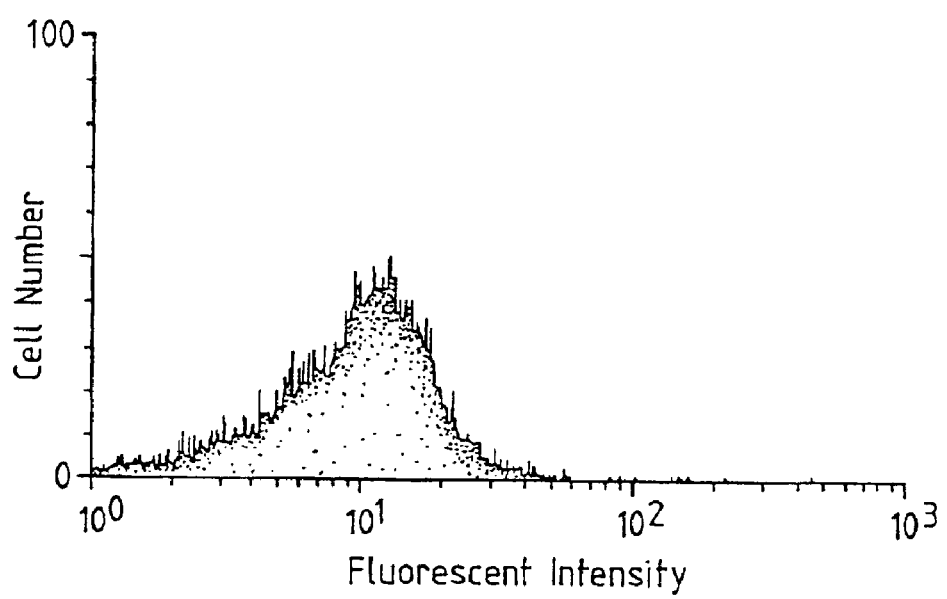

The above procedure was carried out initially using a 9.8 Kb plasmid, containing the murine Moloney Leukemia Virus promoter and the β-galactosidase gene, a reporter gene. On day 8 after transfection the β-galactosidase product was analyzed by FACS-FDG stain after the inhibition of the endogenous β-galactosidase (Reagents and Protocol, Molecular Probes, USA). As shown in FIGS. 6a and 6b, where cell number as a percentage is expressed on the vertical axis against fluorescent intensity on the horizontal axis, there was a clear shift of the fluorescein isothiocyanate (FITC) intensity, which indicates a successful transfection of plasmids to human PBMCs.

This procedure, with minor alterations, can be carried out using plasmids of the invention carrying the ribozymal DNA, as shown in Section 9.

5. CXCR4 Ribozymal DNA

Human CXCR4 ribozymal DNA was prepared analogously to human CCR5 ribozymal DNA as in Section 1 above. The CXCR4 DNA sequence is disclosed in B. Federsppiel et al., Genomics 16, 707–712 (1993). The sequence of the forward primer was

```
5'-gccaagcttc tgcagtaata cgactcacta  (SEQ ID NO:6)

tagggccgaa   aggcccctca   ctctgatgag cgcgaaagcg   cgaaacgttg   tcctctg-3
``` and of the reverse primer was

```
5'-taattggatc ctctagaaac gttgtttcgg  (SEQ ID NO:7)

tcctttcgga   cctcatcagc   tctgatttct cagaggacaa   cgtttcgcgc   tttc-3'
```

Figure 12:
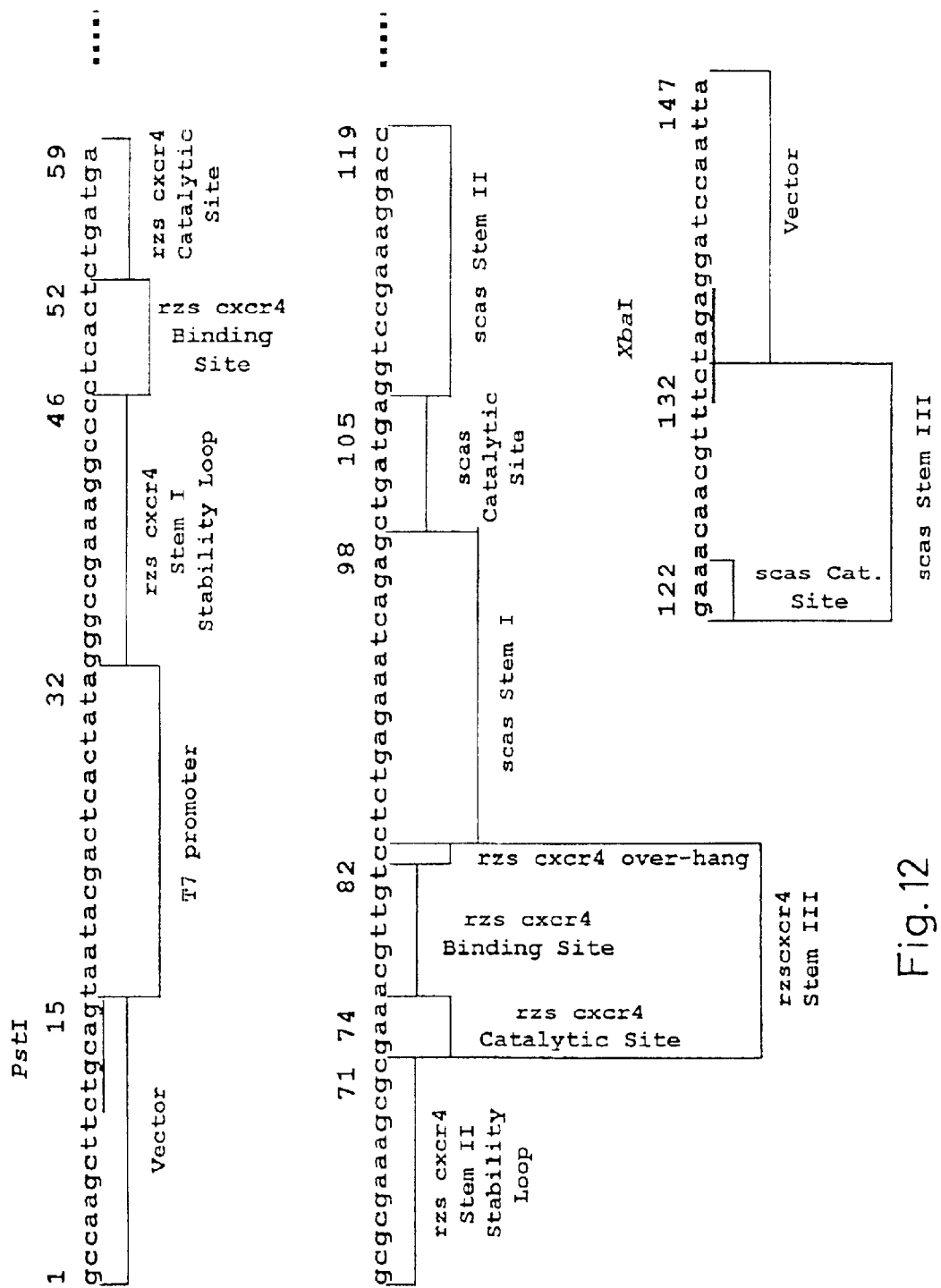

The ribozymal DNA cassette was constructed having the nucleotide sequence SEQ ID NO:8, described more fully in FIG. 12:

```
gccaagcttc   tgcagtaata   cgactcacta tagggccgaa   aggcccctca   ctctgatgag cgcgaaagcg   cgaaacgttg   tcctctgaga aatcagagct   gatgaggtcc   gaaaggaccg aaacaacgtt   tctagaggat   ccaatta         147
```

Referring to FIG. 12, the cassette comprises in order (5' to 3'):

FIG. 12

| Base Nos. | Function |
|---|---|
| 1–15 | Vector sequence. |
| 16–32 | T7 promoter. |
| 33–46 | First structure-stabilising stem loop of the target-cleaving ribozymal DNA ("rzscxcr4 stem I"). |
| 7–52 | First target-recognition sequence (binding site). |
| 53–59 | First catalytic site of the target-cleaving ribozymal DNA. |
| 60–71 | Second structure-stabilising stem loop of the target-cleaving ribozymal DNA ("rzscxcr4 stem II") |
| 72–74 | Second catalytic site of the target-cleaving ribozymal DNA gaa, forming part of stem III ("rzscxcr4 stem III"). |
| 75–82 | Second target-recognition sequence, ending in gu with c overhang, forming the remainder of "rzscxcr4 stem III". |
| 83–98 | First structure-stabilising stem loop of autocatalytic ribozymal DNA ("scas stem I") |
| 99–105 | First scas catalytic site. |
| 106–119 | Second structure-stabilising stem loop of autocatalytic ribozymal DNA ("scas stem II"). |
| 120–132 | Bases gaa forming the scas catalytic site, followed by a 10-base sequence which base-pairs with 10 complementary bases of the second target-recognition sequence and catalytic site above, thus forming another stem ("scas stem III"). |
| 133–147 | Vector sequence. |

6. Engineering of the Polymerase Vector

Referring to FIG. 18, the polymerase vector comprises a promoter from cytomegalovirus (CMV) and the T7 polymerase gene. The complete T7 polymerase DNA sequence is available from Genbank/EMBL under Accession No. M.38308. In this Example, a modified T7 polymerase DNA was obtained and amplified by PCR on plasmid pT7AutoI [J. Dubendorff and F. Studier, J. Mol. Biol. 219, 61–68 (1991)]. The primers used for the PCR incorporated the restriction sites EcoRI and NcoI at the 5' end of the forward primer; and BamHI, at the 5' end of the reverse primer. (BamHI was used later for the cloning of the autopolymerase vector.) The sequences of the primers were as follows with the overlapping T7 polymerase underlined.

```
Forward:
5' acgaattccatggacacgattaacatcg 3' (SEQ ID NO: 9)

EcoRI site = gaattc; NcoI site =
ccatgg

Reverse:
5' atataaggatccttacgcgaacgcgaac 3' (SEQ ID NO: 10)

BamHI site = ggatcc
```

The PCR was carried out using Vent polymerase (which provided a 'blunt end' in the PCR product). The NcoI site introduced by the forward primer is an extra cloning site and was produced by changing the second codon of the T7 polymerase, DNA from an Asn (aac) to an Asp (gac). This does not change the activity of T7 polymerase.

Figure 8:
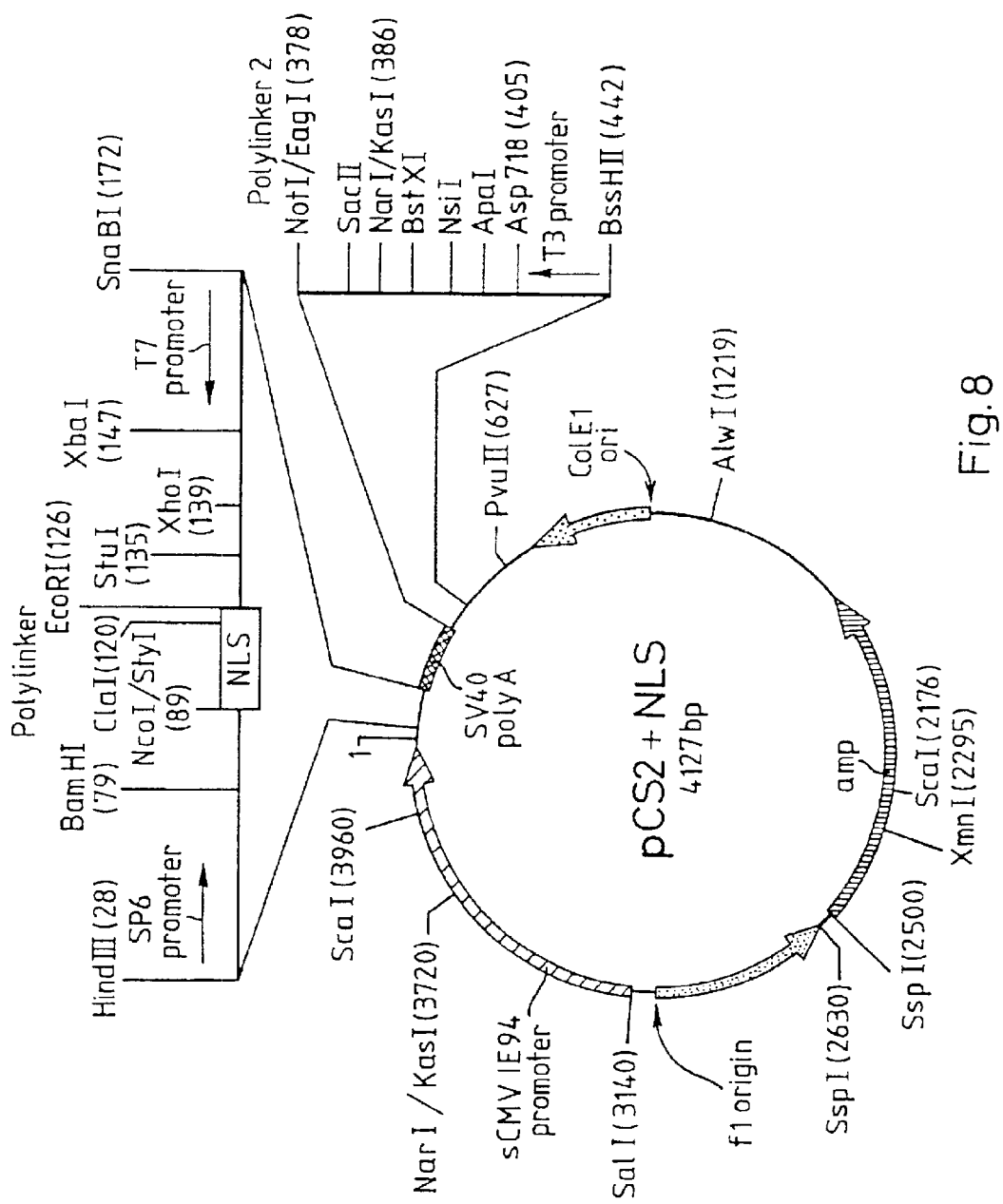
FIG. 8 is a schematic diagram of a plasmid pCS2+NLS used for cloning of T7 polymerase DNA.
Figure 9:
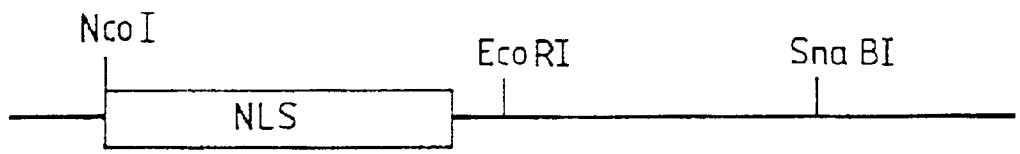
FIG. 9 shows diagrammatically some detail of the operations required for cloning of T7 polymerase in plasmid pCS2+NLS of FIG. 8.
Figure 9:
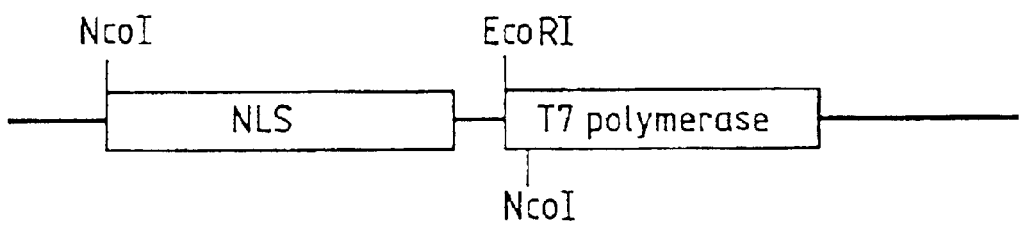
Figure 9:
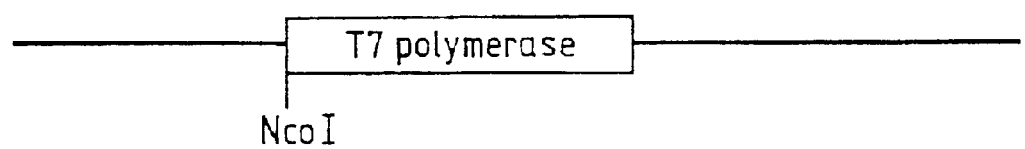
Figure 10:
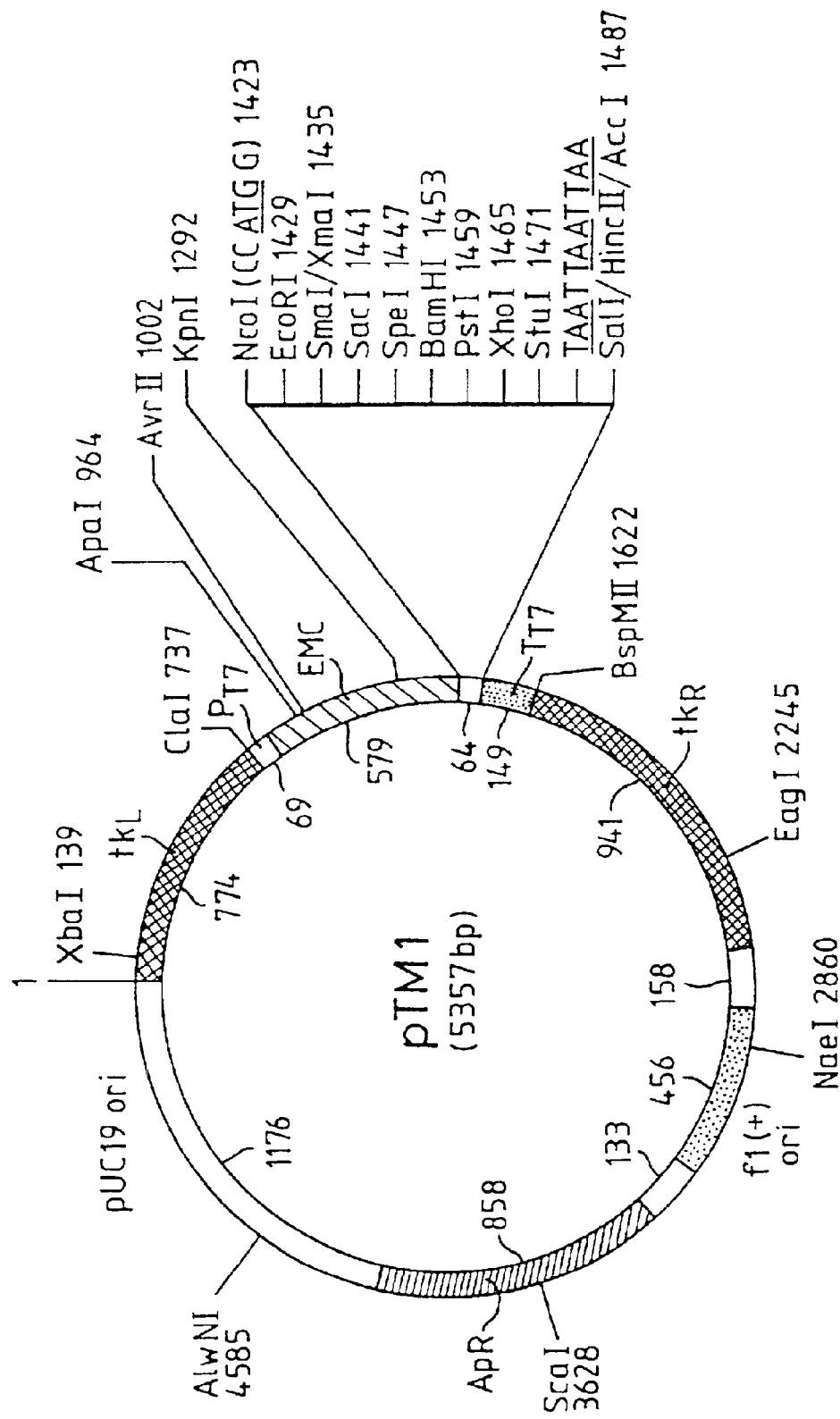
FIG. 10 is a schematic diagram of a plasmid pTM1 containing an internal ribosomal entry site (IRES) from the 5'-untranslated region (UTR) of encephalomyocarditis virus (EMCV)
Figure 11:
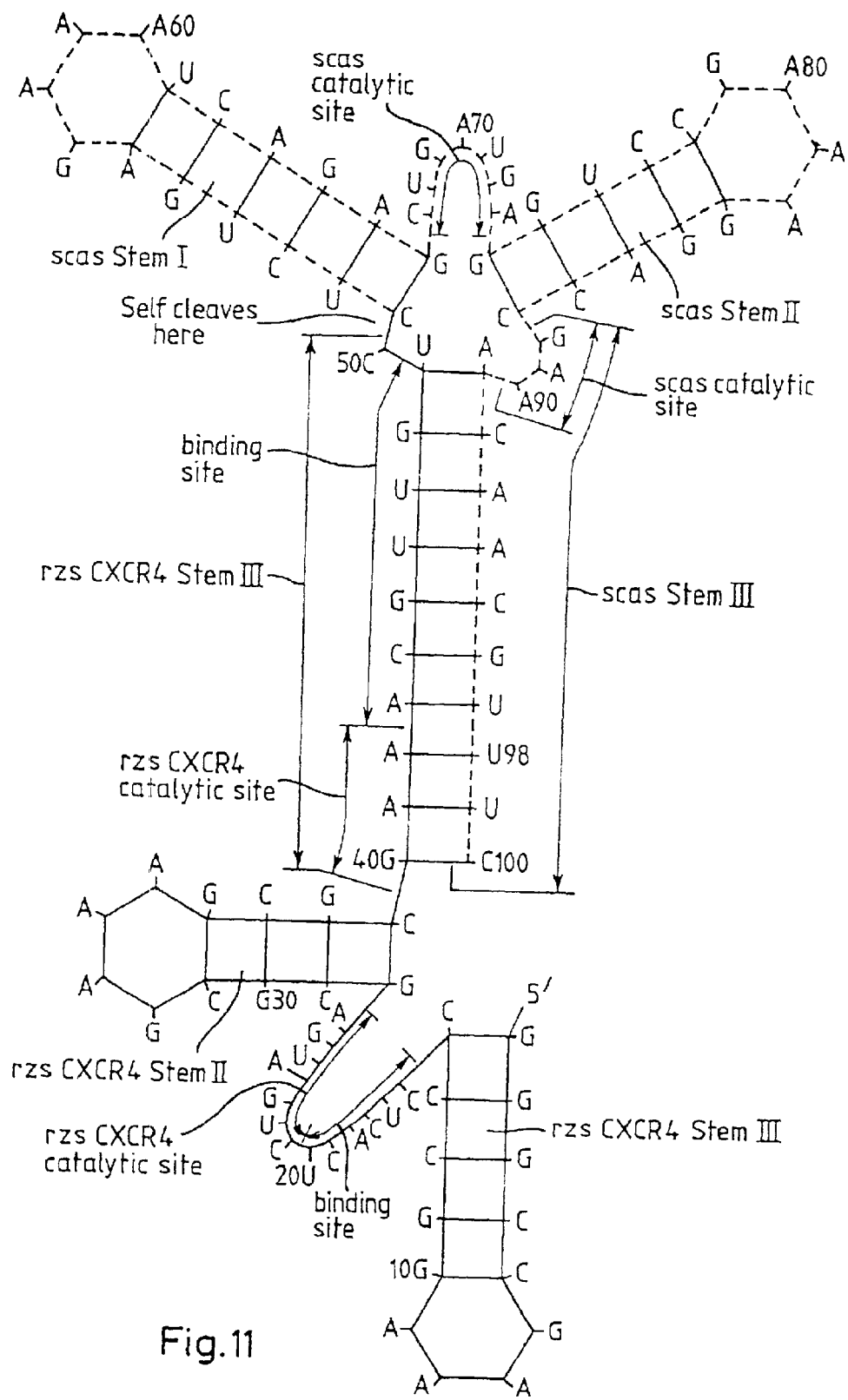

The T7 polymerase PCR product was cloned into a pCS2-NLS plasmid (R. A. W. Rupp et al. Genes and Development 8, 1311–1323 (1994) and D. L. Turner & H. Weintraub ibid. 1434–1447], FIG. 8 is a map of the plasmid pCS2-NLS. The T7 polymerase DNA was introduced into an EcoRI site and a SnaB1 (blunt ended) site in the CS2, located shortly after the NLS in the clockwise direction. The NLS sequence in the pCS2 was unnecessary for the present purpose at this stage and it was deleted by cutting with restriction enzyme NcoI as the NLS sequence was now in between the two NcoI sites. Then the plasmid was religated through the NcoI sites. FIG. 9 explains these operations. Thus the polymerase plasmid vector was completed as shown in FIG. 18. It contained a CMV promoter (already existing in the CS2 vector), which switched on the production of T7 polymerase. T7 polymerase is required for the ribozymal DNA vector and the autopolymerase vector, detailed below.

7. Engineering of the Autopolymerase Vector

The purpose of this vector was to provide a steady and adequate supply of T7 polymerase. The T7 promoter was used to switch on the production of T7 polymerase. This polymerase acted autocatalytically making more T7 promoter which made more T7 polymerase (FIG. 18).

mRNAs made by transfected vectors through non-mammalian promoters in mammalian cell cytoplasm are not usually recognised by the cells for translation into proteins. In order to trick the cell into translating the T7 polymerase mRNA transcribed by the promoter, an encephalomyocarditis (EMC) virus, UTR (untranslated region) sequence, (Moss et al., Nature 348, 91–92 (1990)) was added. This sequence serves as a translational enhancer, providing binding sites for ribosomes and was obtained by PCR-amplifying EMC UTR from the pTM1 vector, see B. Moss et al., Nature 348, 91–92 (1990). The primers used included an XbaI restriction site in the forward strand. No restriction site was introduced in the reverse primer, since the EMC sequence obtained from this vector contained several engineered restriction sites, such as BamHI and NcoI. The primers were as follows, with the overlapping EMC sequences underlined:

```
Forward:
5' gctctagaccacaacggtttccctctag 3' (SEQ ID NO: 11)

XbaI Site = tctaga,

Reverse:
5' cagcttcctttcgggctttgttagcagc 3' (SEQ ID NO: 12)
```

The EMC sequence was then cloned into pET11a (Novagen Ltd.) using XbaI and BamHI sites. For a map, see e.g. the 1996/97 catalogue of R & D Systems Ltd., Abingdon, Oxfordshire, England. page 74. The EMC UTR sequence naturally contained a NcoI restriction site at its 3' end, in front of a BamHI site. Thus, the T7 polymerase sequence, as described above in Section 6, which contained NcoI and BamHI sites, was readily cloned into the plasmid downstream of the EMC UTR sequence, as described by X. Chen et al., Nucleic Acids Research 22, 2114–2120 (1994).

8. Engineering of the Ribozyme Vectors

The cassettes containing the complete ribozymal DNA and T7 promoter were cloned into the well known plasmid pUC19. For one set of experiments, human CCR5 ribozymal DNA was cloned into the plasmid using XbaI and EcoRI sites. For another set of experiments, the CXCR4 cassette was cloned into same plasmid just in front of the CCR5 cassette. This was done using PstI and XhaI restriction enzymes. The CXCR4 cassette has a PstI site near its 5'-end and an XbaI site near its 3'-end (FIG. 12). Restriction with XbaI carries the 3'-end of the CXCR4 cassette to be ligated directly onto the XbaI site near the 5'-end of the CCR5 cassette (FIG. 3). The resultant plasmids conform to the "ribozyme vector" shown in FIG. 18.

9. Expression of the Vectors in Human Peripheral Blood Mononuclear Cells, Showing Powerful Inhibition of CCR5 and CXCR4 RNA Human peripheral blood mononuclear cells (PBMC) were isolated and cultured as described in Section 1. Various of the three vectors, i.e. polymerase, autopolymerase and ribozymal DNA, as shown in FIG. 18, were added in equal proportions for transfection. Three experiments were carried out (1) in which all three vectors were added, (2) in which only the polymerase vector and ribozymal DNA vector were added and (3) in which only the polymerase vector was added.

Transfection was carried out as described by Gibco Ltd. which supplied DMRIE-C reagent. 8 μl of DMRIE-C was mixed with 4 μg in 1 ml of Optic-MEM before $2 \times 10^6$ cells were added for transfection, as described by Gibco's instructions. Cells were then stimulated with PHA-L (Sigma) at 1 μg/ml and IL-2 10 U/ml for 48 hours (final volume, 3 ml) before they were harvested for analysis. In a first set of experiments, the ribozymal DNA plasmid containing only CCR5 ribozymal DNA was used. In a second set of experiments the PBMC were transfected with a plasmid containing both CXCR4 and CCR5 ribozymal DNA in a single plasmid (FIG. 18, Section 8 above).

RNA was isolated from the transfected cells as described in Section 1 and PCR was carried out to identify cellular CCR5 or CXCR4 mRNA using the above-described CCR5 or CXCR4 primer. Also, as the cells naturally express actin, the amount of mRNA of actin provides a quantitative control. Such a control confirms that the inhibition of CCR5 and/or CXCR4 is not due to the general degradation of RNA; otherwise the actin RNA would have degraded too. It also confirms that the ribozyme action is specific, in that it does not cleave actin RNA. This control, using actin, is widely applied in molecular biology.

Figure 13A:
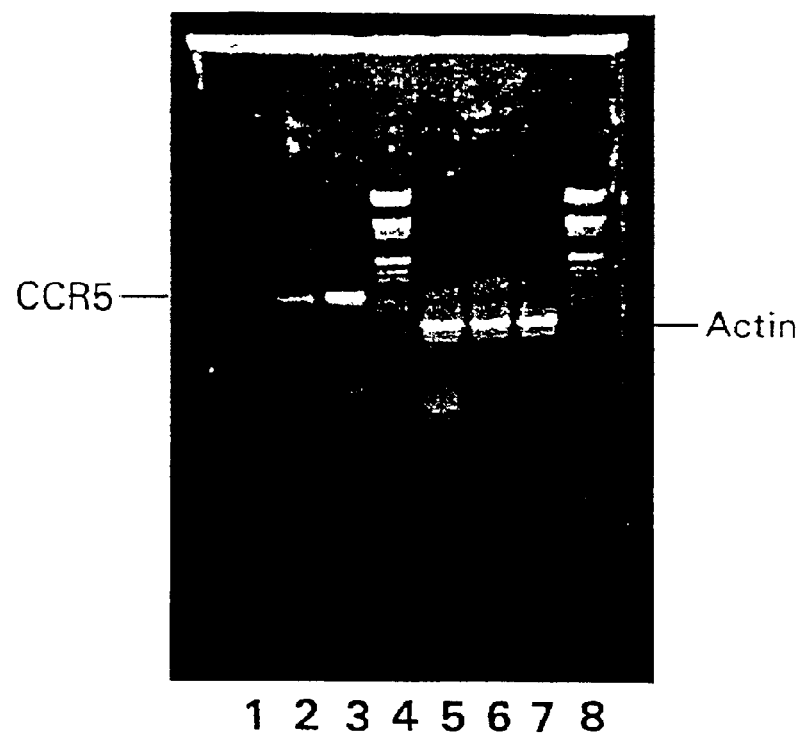
FIGS. 13a, 13b and 14 are photographs of agarose gels containing fragments of RNA transcribed from human peripheral mononuclear cells which have been transfected with ribozymes of the invention.
Figure 13B:
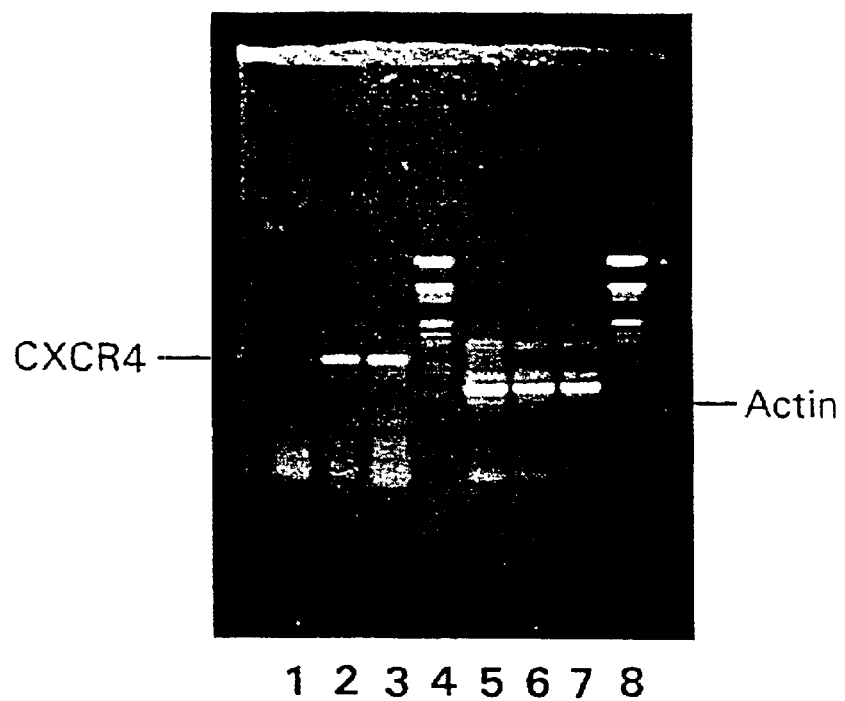
Figure 14:
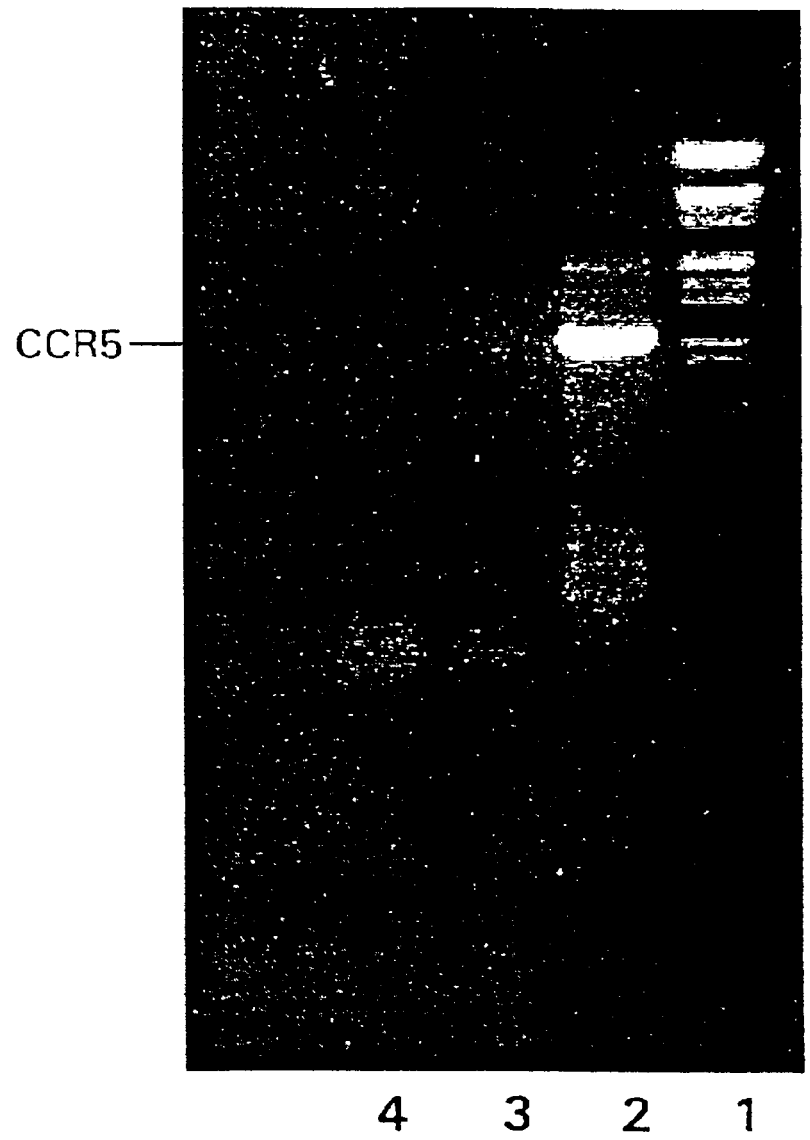
Figure 15A:
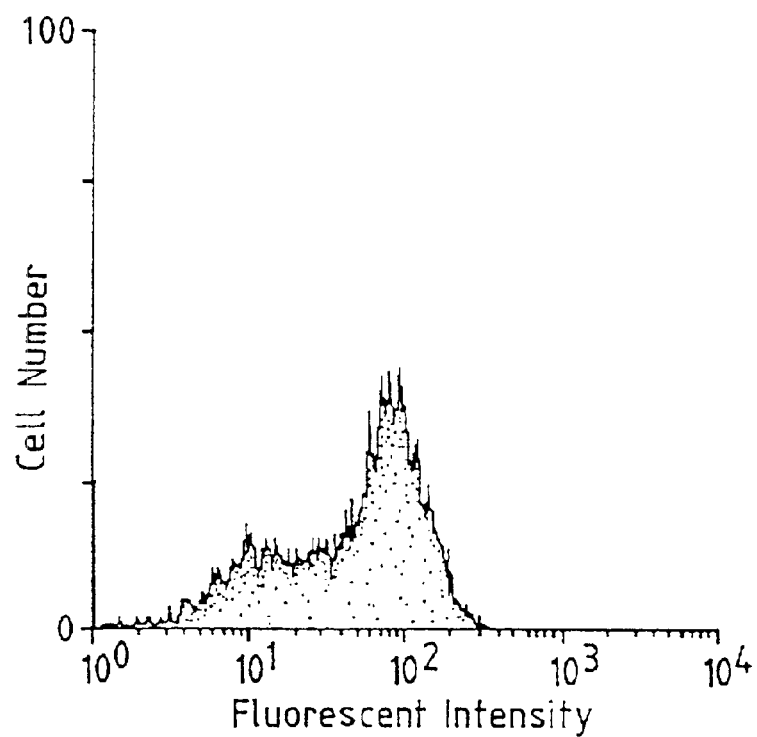
Figure 15B:
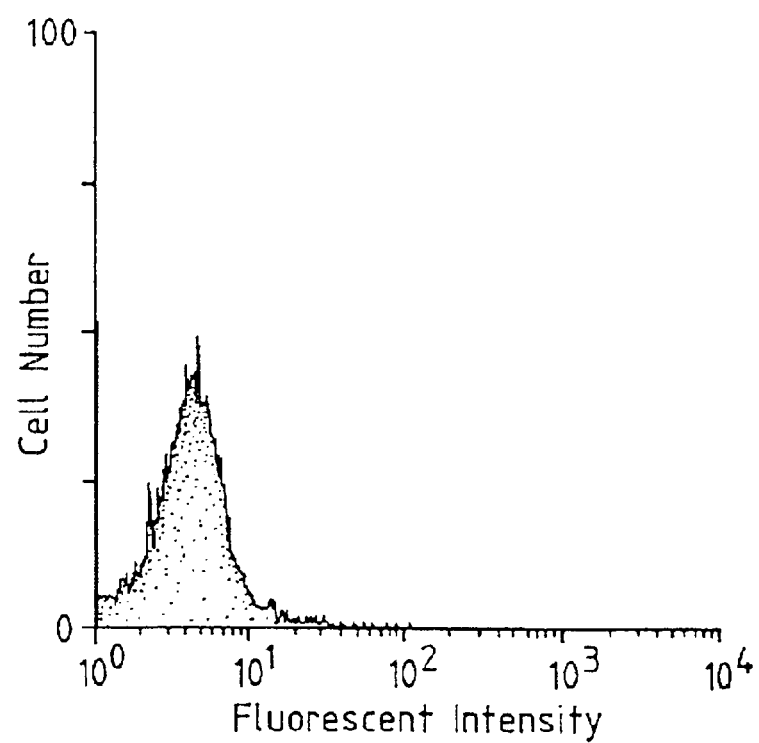

The results are shown in FIGS. 13a, 13b and 14 which are stained agarose gel photographs of the relevant PCR products. FIGS. 13a and 13b relate, respectively, to the first and second sets of experiments, FIG. 13a showing the action of the ribozyme against CCR5 RNA and 13b showing the action against CXCR4 RNA. The arrangement of FIGS. 13a and 13b is the same, and is as follows, numbering the lanes 1–8 left to right:

| mRNA type | Lane No. | Polymerase vector present in vector system | Autopolymerase vector present in vector system | Ribozymal DNA vector present in vector system |
| --- | --- | --- | --- | --- |
| CCR5 or CXCR4 | 1 | Yes | Yes | Yes |
| " | 2 | Yes | No | Yes |
| " | 3 | Yes | No | No |
| " | 4 | [Molecular weight markers] | | |
| Actin | 5 | Yes | Yes | Yes |
| " | 6 | Yes | No | Yes |
| " | 7 | Yes | No | No |
| " | 8 | [Molecular weight markers] | | |

Lane 1 shows that CCR5 and mRNA was not deletable from the PBMC transfected with all three vectors, i.e. the polymerase, the autopolymerase and the ribozymal DNA vectors, thus indicating complete inhibition of CCR5 mRNA. Lane 2 contains a weak band of CCR5 mRNA, showing that without the autopolymerase vector, the inhibition of CCR5 and CXCR4 mRNA was incomplete. Lane 3 contains a bright band of the CCR5 or CXCR4 RNA, showing that without the ribozyme vector there is no inhibition of CCR5 (FIG. 13a) or CXCR4 (FIG. 13b) mRNA. The inhibition of the CCR5 or CXCR4 RNA was specific, as the controls in Lanes 5–7 show clearly a bright band of actin mRNA from the same transfected cells as in Lanes 1–3. Thus, specific and powerful inhibition of CCR5 and CXCR4 has been achieved by the present invention. Although the powerful inhibition required the autopolymerase vector, those skilled in the art will be able to devise alternative ways of boosting ribozymal production to equivalent or greater levels. This can be done by increasing the concentration of the ribozymes using for instance, multicopies of ribozymal DNA sequence in the vector or vectors and/or by increasing the amount and/or efficiency of promoters.

All of the T7-related work described herein followed the protocols and recommendations by Novagen Ltd, including pLysS gel purification. The rest followed the protocols in "Molecular Cloning—A Laboratory Manual", $2^{nd}$ ed. 1989 ed. Sambrook, Fritzsch and Maniatis.

As mentioned earlier, the ribozymal DNA vector containing CXCR4 ribozymal DNA also contains CCR5 ribozymal DNA. The mRNA level of CCR5 from PBMCs treated with this vector was monitored and the result is shown in FIG. 14. Referring to FIG. 14, lanes are numbered right to left. Lane 1 is molecular weight markers, Lane 2 containing a large bright band, is PBMCs treated with a control vector CS2 containing no ribozyme. Lane 3 shows PBMCs treated with polymerase and ribozymal DNA vectors only, Lane 4 with polymerase, autopolymerase and ribozymal DNA vectors. A complete cleavage is seen, as indicated by the disappearance of the CCR5 band. This has also provided clear evidence that the self-cleaving, ribozyme is capable of producing multiple ribozymes from the same vector.

Figure 16A:
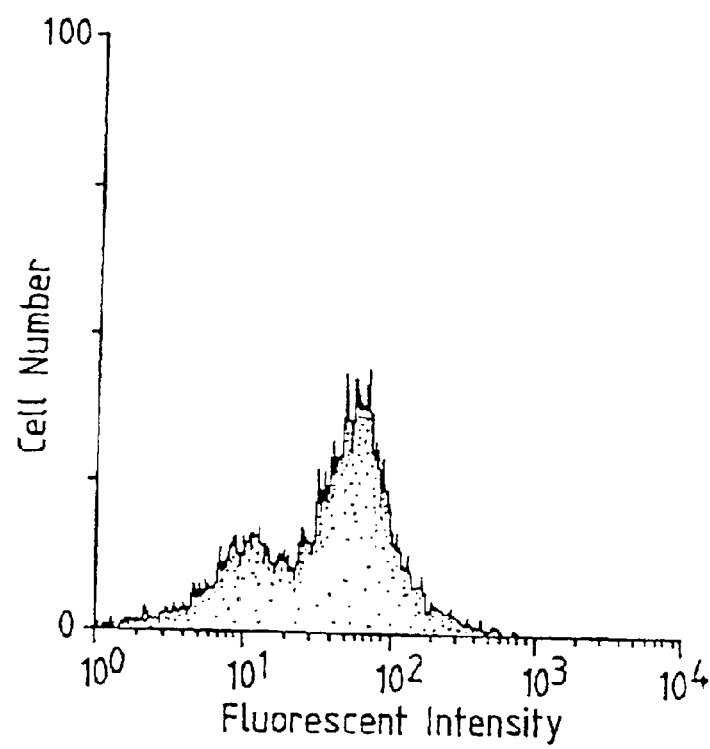
Figure 16B:
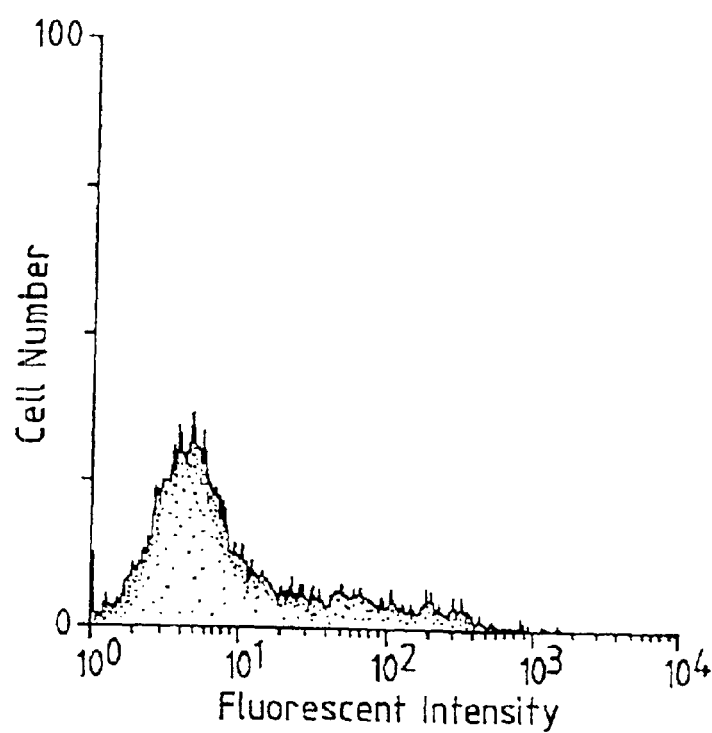

10. Effects on PBMC Cellular Expression of CCR5 and CXCR4 Protein Molecules after Treatment with Ribozymes Following the transfection as described in Section 9, human PBMCs from individual donors (un-pooled) were stimulated with PHA-L and IL-2 as described in Section 4 or stimulated with a monoclonal antibody to CD3 called UCHT-1 (available from Dept. of Immunology, University College Hospital, London, UK) with IL-2 at 10 U/ml as described by Masseyeff et al. in "Methods of Immunological Analysis" (pub. VCH Verlag, Weinheim Germany (1993)). The cells were stained at days 3, 5, 7, 10, 12 with monoclonal antibodies to CCR5 or CXCR4 or control antibodies which were directly conjugated with fluorescent materials, commercially available from PharMingen Ltd. The staining procedure followed the instructions from the same company. The data were analysed using a Fluorescent Activated Cell Sorter (Becton Dickinson Ltd) as in Section 4. The results are summarised below as well as in FIGS. 16a, 16b (CCR5) and 17a, 17b (CXCR4). Those Figures are similar to FIGS. 6a and 6b referred to in Section 4. Here they show a clear shift of cell population to the left, indicating decrease in the expression of CCR5 or CXCR4.

The best inhibition was seen on different days in each different individual. On average, CCR5 ribozyme inhibited 78% of the expression of CCR5. CXCR4 ribozyme (which also contained CCR5 ribozyme) inhibited CXCR4 expression by 69% and CCR5 expression by 79%.

11. Inhibition of HIV Infection in Human Peripheral Blood Mononuclear Cells (PBMCs) Treated with the Ribozymes Following the transfection as described in Section 9, the cells were stimulated with PHA-L and IL-2 as described in Section 4. These cells were pelleted on day 5 before the incubation with 100 µl of a HIV strain called LAI, available from MRC (Medical Research Council, UK). It contained 3000 pg of p24 HIV surface antigen protein, as determined by sandwich ELISA supplied by Coulter Ltd. (This is the same assay used clinically to determine the amount of virus in patients' blood.) The mixture was then incubated at 37° C. for 2 hours with 5% $CO_2$. The suspension was washed with RPMI1640 (Gibco Ltd.) thrice, centrifuging at using 200 g. Then, 1 million cells were resuspended in 4 ml RPMI1640 culture medium, as described before, containing 10% foetal calf serum and 10 U/ml IL-2. 3–4 days later IL-2 was topped up to 10 U/ml. The culture supernatants were harvested at day 7 after the infection. Sandwich ELISA as mentioned above was used to determine the amount of p24, giving a direct indication of the amount of virus. The culture supernatants were diluted at 1:100 and 1:500 for the assay in order to obtain data in pg/ml within the reliable calibration region of the standard curve of the ELISA. The results are as follows.

| Cell Treatment | Amount of p24 (pg/ml) | |
|---|---|---|
| | Experiment 1 | Experiment 2 |
| Untransfected cells | 18,553 | 7,755 |
| Cells transfected with polymerase, autopolymerase and CXCR4 ribozymal DNA vectors (3 vectors): | Not detectable | Not detectable |

The above data show clearly that all HIV infectivity was inhibited by the treatment with the ribozymal vector system.

All the prior references cited herein for the purpose of referring to known materials, sequences and procedures are hereby expressly incorporated herein by reference to the extent of describing the materials, sequences and procedures referred to.

Sequence Listing Free Text

Sequences deemed "artificial" for the purposes of Sequence Listing contain free text under identifier <223> as follows:

| SEQ ID NO: | Free text description following "Description of Artificial Sequence" |
|---|---|
| 4 | DNA cassette containing T7 promoter and ribozymal DNA targeting CCR5 |
| 8 | DNA cassette containing T7 promoter and ribozymal DNA targeting CXCR4 |
| 9 & 10 | PCR primer containing T7 polymerase sequence |
| 11 & 12 | PCR primer containing encephalomyocarditis vurus (EMCV) 5'-UTR sequence |

What is claimed is:

1. A vector system comprising at least one DNA vector, the vector or vectors containing a target-cleaving hammerhead ribozymal DNA sequence under control of a promoter effective in human cells and which, upon transcription to RNA cleaves the mRNA transcribed from a target gene encoding the CCR5 or CXCR4 protein, wherein the said target-cleaving ribozymal DNA sequence comprises a first recognition sequence (5' to 3') complementary to CCR5 or CXCR4 mRNA:

tagattg or ctcact, respectively for CCR5 and CXCR4 and downstream thereof a second recognition sequence acttg or acgttgt, respectively for CCR5 and CXCR4.

2. A The vector system according to claim 1, containing target-cleaving ribozymal sequences for cleaving mRNA transcribed from both the CCR5 and CXCR4 target genes.

3. A The vector system according to claim 1, comprising at least two DNA vectors, wherein a first vector contains a first promoter effective in human cells, operably linked to a gene which is expressible to produce an activator protein capable of acting on a second promoter, and a second vector contains the second promoter operably linked to a target-cleaving hammerhead ribozymal DNA sequence for cleaving mRNA transcribed from the CCR5 target gene, the CXCR4 target gene or both the CCR5 and CXCR4 target genes, wherein the second promoter is a T7 polymerase promoter and the activator protein is a T7polymerase.

4. The vector system according to claim 3, comprising at least 3 DNA vectors, wherein the second vector contains target-cleaving ribozymal DNA for cleaving mRNA transcribed from the CCR5 target gene and wherein the third vector contains target-cleaving ribozymal DNA for cleaving mRNA transcribed from the CXCR4 target gene.

5. The vector system according to claim 3, which further comprises DNA providing an internal ribosome entry site (IRES) for assisting the translation of the T7 polymerase gene in human cells.

6. A The vector system according to claim 1 wherein the ribozymal DNA sequence further comprises, downstream of the target-cleaving ribozymal sequence, a 3'-autocatalytic hammerhead ribozymal DNA sequence, so that when the ribozymal DNA is transcribed to RNA, it forms as a double hammerhead, having first and second stems of a target-cleaving ribozyme which targets CCR5 or CXCR4 mRNA and first and second stems of 3'-autocatalytic ribozyme.

7. A The vector system according to claim 1, wherein a first and second structure-stabilising stem loop is positioned one to each side of the first recognition sequence.

8. The vector system according to claim 7, wherein a second recognition sequence is positioned downstream of the second structure-stabilising stem loop.

9. The vector system acid according to claim 8, wherein the target-cleaving ribozyme sequence comprises in order (5' to 3'):

a first structure-stabilising stem loop;

a first target-recognition sequence;

a first catalytic sequence;

a second structure-stabilising stem loop;

a second catalytic sequence; and a second target-recognition sequence.

10. Ribozymal DNA comprising (1) a target-cleaving hammerhead ribozymal DNA sequence under control of a promoter effective in human cells and which, upon transcription to RNA will cleave the mRNA transcribed from a target gene encoding the CCR5 or CXCR4 protein, and downstream thereof (2) a 3'-autocatalytic hammerhead ribozymal DNA sequence, so that when the ribozymal DNA is transcribed to RNA, it forms as a double hammerhead; having first and second stems of a target-cleaving ribozyme which targets CCR5 or CXCR4 mRNA and first and second stems of 3'-autocatalytic ribozyme, together with a common third stem joining the two hammerheads, the target-cleaving ribozymal DNA sequence, when transcribed to RNA, cleaving a target RNA sequence present in CCR5 or CXCR4 RNA, and wherein the target-cleaving ribozymal DNA sequence comprises a first recognition sequence (5' to 3'):

tagattg or ctcact, respectively for CCR5 and CXCR4 and downstream thereof a second recognition sequence acttg or acgttgt, respectively for CCR5 and CXCR4.

11. A ribozymal DNA which, when transcribed to RNA cleaves a target RNA sequence present in CCR5 or CXCR4 RNA and which contains a first recognition sequence (5' to 3'):

tagattg or ctcact, respectively for CCR5 and CXCR4 and downstream thereof a second recognition sequence acttg or acgttgt, respectively, for CCR5 and CXCR4.

12. A ribozymal DNA according to claim 11 comprising tandem CCR5 RNA- and CXCR4 RNA-cleaving sequences.

* * * * *

UNITED STATES PATENT AND TRADEMARK OFFICE
CERTIFICATE OF CORRECTION

PATENT NO.         : 6,916,653 B2                                      Page 1 of 1
APPLICATION NO.   : 09/880821
DATED              : July 12, 2005
INVENTOR(S)        : Eagles et al.

It is certified that error appears in the above-identified patent and that said Letters Patent is hereby corrected as shown below:

Title page,
Item [63], Related U.S. Application Data, delete "No. PCT/GB99/00134, filed on Jan. 15, 1998", and insert -- No. PCT/GB99/00134, filed on Jan. 15, 1999 --.

Signed and Sealed this

Twentieth Day of June, 2006

JON W. DUDAS
*Director of the United States Patent and Trademark Office*

SEQUENCE LISTING

<160> NUMBER OF SEQ ID NOS: 15

<210> SEQ ID NO 1
<211> LENGTH: 13
<212> TYPE: RNA
<213> ORGANISM: Artificial Sequence
<220> FEATURE:
<223> OTHER INFORMATION: Description of Artificial Sequence: Synthetic
      target sequence CCR5

<400> SEQUENCE: 1
caaguccaau cua                                                          13

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: Synthetic
      target sequence CXCR4

<400> SEQUENCE: 2
acaacgucag ugag                                                         14

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcacagggt ggaacaagat                                                   20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacttgagtc cgtgtcacaa gc                                                22

<210> SEQ ID NO 5
<211> LENGTH: 137
<212> TYPE: DNA
<213> ORGANISM: Artificial Sequence
<220> FEATURE:
<223> OTHER INFORMATION: Description of Artificial Sequence: Synthetic
      ribozymal DNA cassette

<400> SEQUENCE: 5
aatctagagg atcctaatac gactcactat agggcgaaag ccctagattg ctgatgagcg       60
cgaaagcgcg aaacttgtcc tctacgaaag tagagctgat gagaccgaaa ggtcgaaaca      120
agtgagctcg aattctt                                                     137

<210> SEQ ID NO 6
<211> LENGTH: 87
<212> TYPE: DNA
<213> ORGANISM: Artificial Sequence
<220> FEATURE:

-continued

<223> OTHER INFORMATION: Description of Artificial Sequence: Synthetic
     primer

<400> SEQUENCE: 6
gccaagcttc tgcagtaata cgactcacta tagggccgaa aggcccctca ctctgatgag     60
cgcgaaagcg cgaaacgttg tcctctg                                        87

<210> SEQ ID NO 7
<211> LENGTH: 84
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
taattggatc ctctagaaac gttgtttcgg tcctttcgga cctcatcagc tctgatttct     60
cagaggacaa cgtttcgcgc tttc                                           84

<210> SEQ ID NO 8
<211> LENGTH: 147
<212> TYPE: DNA
<213> ORGANISM: Artificial Sequence
<220> FEATURE:
<223> OTHER INFORMATION: Description of Artificial Sequence: Synthetic
     ribozymal DNA cassette

<400> SEQUENCE: 8
gccaagcttc tgcagtaata cgactcacta tagggccgaa aggcccctca ctctgatgag     60
cgcgaaagcg cgaaacgttg tcctctgaga atcagagct gatgaggtcc gaaaggaccg    120
aaacaacgtt tctagaggat ccaatta                                       147

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
acgaattcca tggacacgat taacatcg                                       28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
atataaggat ccttacgcga acgcgaac                                       28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
gctctagacc acaacggttt ccctctag                                       28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagcttcctt tcgggctttg ttagcagc                                          28

<210> SEQ ID NO 13
<211> LENGTH: 48
<212> TYPE: RNA
<213> ORGANISM: Artificial Sequence
<220> FEATURE:
<223> OTHER INFORMATION: Description of Artificial Sequence: Synthetic
      CCR5 ribozyme sequence

<400> SEQUENCE: 13
gggcgaaagc ccuagauugc ugaugagcgc gaaagcgcga aacuuguc                    48

<210> SEQ ID NO 14
<211> LENGTH: 93
<212> TYPE: RNA
<213> ORGANISM: Artificial Sequence
<220> FEATURE:
<223> OTHER INFORMATION: Description of Artificial Sequence: Synthetic
      ribozyme sequence

<400> SEQUENCE: 14
gggcgaaagc ccuagauugc ugaugagcgc gaaagcgcga aacuuguccu cuacgaaagu       60
agagcugaug agaccgaaag gucgaaacaa gug                                    93

<210> SEQ ID NO 15
<211> LENGTH: 100
<212> TYPE: RNA
<213> ORGANISM: Artificial Sequence
<220> FEATURE:
<223> OTHER INFORMATION: Description of Artificial Sequence: Synthetic
      ribozyme sequence

<400> SEQUENCE: 15
gggccgaaag gccccucacu cugaugagcg cgaaagcgcg aaacguuguc cucugagaaa       60
ucagagcuga ugagguccga aaggaccgaa acaacguuuc                            100